(12) United States Patent
Yang et al.

(10) Patent No.: US 8,440,168 B2
(45) Date of Patent: May 14, 2013

(54) IMAGE-GUIDED THERAPY OF MYOCARDIAL DISEASE: COMPOSITION, MANUFACTURING AND APPLICATIONS

(75) Inventors: David J. Yang, Sugar Land, TX (US); Chang-Sok Oh, Houston, TX (US); Saady Kohanim, Sugar Land, TX (US); Dong-Fang Yu, Houston, TX (US); Richard Mendez, Houston, TX (US); E. Edmund Kim, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1017 days.

(21) Appl. No.: 12/340,338

(22) Filed: Dec. 19, 2008

(65) Prior Publication Data

US 2009/0238756 A1 Sep. 24, 2009

Related U.S. Application Data

(60) Provisional application No. 61/038,973, filed on Mar. 24, 2008.

(51) Int. Cl.
*A61K 51/04* (2006.01)
*A61K 49/00* (2006.01)

(52) U.S. Cl.
USPC ......... 424/1.65; 424/9.36; 424/9.42; 424/9.5; 424/94.5

(58) Field of Classification Search .............. 424/9.2, 424/94.6, 489, 490, 494, 1.65, 9.36, 9.42, 424/9.5; 514/46, 171, 188, 186, 184, 352
See application file for complete search history.

(56) References Cited

U.S. PATENT DOCUMENTS

| | | | |
|---|---|---|---|
| 4,387,103 A | 6/1983 | Erhardt et al. | 514/354 |
| 4,439,356 A | 3/1984 | Khanna et al. | 530/350 |
| 4,556,668 A * | 12/1985 | Erhardt et al. | 514/353 |
| 5,112,595 A | 5/1992 | Woulfe et al. | 424/1.77 |
| 5,188,934 A | 2/1993 | Menchen et al. | 435/6 |
| 6,521,209 B1 | 2/2003 | Meade et al. | 424/9.3 |
| 6,692,724 B1 | 2/2004 | Yang et al. | 424/1.49 |
| 6,770,259 B2 | 8/2004 | Carpenter, Jr. | 424/9.1 |
| 2002/0054852 A1* | 5/2002 | Cate | 424/9.2 |
| 2006/0258652 A1 | 11/2006 | Haj-Yehia et al. | 514/230.5 |
| 2008/0107598 A1 | 5/2008 | Yang et al. | 424/1.73 |
| 2008/0131517 A1* | 6/2008 | Fawzy et al. | 424/494 |
| 2011/0104103 A1* | 5/2011 | Heetebrij et al. | 424/85.2 |

FOREIGN PATENT DOCUMENTS

| | | |
|---|---|---|
| CN | 1867363 | 11/2006 |
| WO | WO 96/00717 | 1/1996 |
| WO | WO 2004/026344 | 4/2004 |

OTHER PUBLICATIONS

Alberico et al., "Imaging in head and neck oncology," *Surg. Oncol. Clin. N. Am.*, 13:13-35, 2004, Abstract.
Dobrucki and Sinusas, "Molecular imaging: a new approach to nuclear cardiology," *The Quarterly Journal of Nuclear Medicine and Molecular Imaging*, 49:106-115, 2005.
Erhardt et al., "Ultra-short-acting beta-adrenergic receptor blocking agents. 2. (Aryloxy)propanolamines containing esters on the aryl function," *J. Med. Chem.*, 25:1408-1412, 1982.
Galderisi et al., "Doppler echocardiography and myocardial dyssynchrony: a practical update of old and new ultrasound technologies," *Cardiovascular Ultrasound*, 5:28, 2007.
Henson et al., "Gadolinium-enhanced CT angiography of the circle of Willis and neck," *AJNR Am. J Neuroradiol.*, 25:969-972, 2004.
Heusch et al., "α-adrenergic coronary vasoconstriction and myocardial inschemia in humans," *Circulation*, 101:689-694, 2000.
Hockings et al., "Effect of beta adrenergic blockade on thallium-201 myocardial perfusion imaging," *Br. Heart J.*, 49:83-9, 1983.
Ronda et al., "Polymerization of phenlglysidylether derivatives with functional ester groups," *Reactive & Functional Polymers*, 28:1-11, 1995.
Saha et al., "Radiopharmaceuticals for brain imaging," *Semin. Nucl. Med.*, 24:324-349, 1994, Abstract.
Strunk and Schild, "Actual clinical use of gadolinium-chelates for non-MRI applications," *Eur. Radiol.*, 14:1055-1062, 2004.
Walker et al., "Dipyridamole combined with exercise for thallium-201 myocardial imaging," *Br. Heart J.*, 55:321-9, 1986.
International Search Report and Written Opinion, issued in Application No. PCT/US2008/087777, date of mailing Jul. 30, 2009.
English Translation of office communication issued in corresponding Chinese Patent Application No. 200880128867.8, dated Apr. 17, 2012.

* cited by examiner

*Primary Examiner* — Michael G Hartley
*Assistant Examiner* — Jagadishwar Samala
(74) *Attorney, Agent, or Firm* — Parker Highlander PLLC

(57) ABSTRACT

Compositions and methods for imaging and for chemotherapy and radiotherapy are disclosed. More particularly, the invention concerns agents comprising a targeting moeity comprising a beta-adrenergic receptor targeting compound conjugated or embedded with ethylenediamine. The present invention also concerns methods of application of such agents for imaging and treatment of cardiovascular diseases, and kits for preparing a radiolabeled therapeutic or diagnostic agent.

17 Claims, 12 Drawing Sheets

IMAGE-GUIDED THERAPY OF MYOCARDIAL DISEASE: COMPOSITION, MANUFACTURING AND APPLICATIONS

BACKGROUND OF THE INVENTION

This application claims priority to U.S. Provisional Patent Application Ser. No. 61/038,973 filed Mar. 24, 2008, which is incorporated herein by reference in its entirety.

I. Field of the Invention

The present invention relates generally to the fields of radioimaging, radiotherapy, labeling, chemotherapy, and chemical synthesis. More particularly, the invention concerns certain novel agents suitable for imaging and therapy of heart diseases.

II. Background and Description of Related Art

Cardiovascular disease (CVD) is the leading cause of death in most Western countries and encompasses dysfunctional conditions of the heart, arteries, veins and lungs that supply oxygen to vital life-sustaining areas of the body like the brain, the heart itself, and other vital organs. In the US, nearly one in two Americans dies of some form of cardiovascular disease, the annual toll coming to more than 975,000. Cardiovascular diseases can include coronary heart disease (CHD), coronary artery disease (CAD), chronic obstructive pulmonary disease (COPD), atherosclerosis, intrinsic cardiomyopathies (CM), and thrombosis, and can lead to potentially life-threatening events such as heart failure, myocardial infarction, pulmonary embolism and stroke.

Biomedical imaging includes various modalities that are widely used by physicians and researchers in assessing cardiovascular disease and more recently, in directing therapeutic approaches. By combining a variety of such techniques into clinical protocols, key functional and morphological features of cardiovascular system function or dysfunction can be assessed. Providing a detailed a picture of cardiovascular function to health care professionals is critical for treatment and for early and accurate diagnoses. Early diagnosis of cardiovascular disease is, as with many disease conditions, important for maximizing treatment effectiveness and minimizing long-term health impacts. More importantly for some forms of cardiovascular disease, it provides patients with time to make healthy lifestyle changes as well as a better chance of improving their prognosis through such efforts.

Owing to the widespread incidence of cardiovascular diseases, their often deadly outcomes, and the potential benefits for patients with early diagnosis, there remains a need for additional diagnostic tools and treatment options for many forms of cardiovascular dysfunction.

SUMMARY OF THE INVENTION

The inventors have synthesized certain chemical conjugates that can be applied as novel diagnostic and therapeutic agents. In accordance with certain aspects of the present invention, there is provided an agent comprising a targeting moeity comprising a beta-adrenergic receptor targeting compound conjugated or embedded with ethylenediamine. Conjugation may refer to a chemical bond or coupling of moieties via a linker. A beta-adrenergic receptor targeting compound includes, but is not limited to, AC 623, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, butidrine hydrocholoride, butofilolol, carazolol, carteolol, carvedilol, celiprolol, cetamolol, cloranolol, dilevalol, esmolol, indenolol, labetalol, landiolol, levobunolol, mepindolol, metipranolol, metoprolol, moprolol, nadolol, nadoxolol, nebivolol, nifenalol, nipradilol, oxprenolol, penbutolol, pindolol, practolol, pronethalol, propranolol, sotalol, sulfinalol, talinolol, tertatolol, tilisolol, timolol, toliprolol, xibenolol and combinations thereof. In certain embodiment, the beta-adrenergic receptor targeting compound is esmolol.

Examples of appropriate linking methodologies for chemical conjugates are provided in U.S. Pat. Nos. 4,439,356 and 5,188,934; U.S. Publication 2003/0194740; European Patent Application 87310256.0; International Application PCT/US90/05565, each of which is incorporated herein by reference in its entirety. A "linker" refers to a single covalent bond or a moiety comprising series of stable covalent bonds, the moiety often incorporating 1-40 plural valent atoms selected from the group consisting of C, N, O, S and P that covalently attach a reporter moiety to another moiety such as a chemically reactive group or a biological and non-biological component, such as a base moiety. The number of plural valent atoms in a linker may be, for example, 0, 1, 2, 3, 4, 5, 6, 7, 8, 9, 10, 20, 25, 30 or a larger number up to 40 or more. A linker may be linear or non-linear; some linkers have pendant side chains or pendant functional groups (or both). Examples of such pendant moieties are hydrophilicity modifiers, for example solubilizing groups like, e.g., sulfo (—$SO_3H$ or —$SO_3^-$). In one aspect, a linker is composed of any combination of single, double, triple or aromatic carbon-carbon bonds, carbon-nitrogen bonds, nitrogen-nitrogen bonds, carbon-oxygen bonds and carbon-sulfur bonds. Exemplary linking members include a moiety that includes —C(O)NH—, —C(O)O—, —NH—, —S—, —O—, and the like. Linkers may by way of example consist of a combination of moieties selected from alkyl, —C(O)NH—, —C(O)O—, —NH—, —S—, —O—, —C(O)—, —$S(O)_n$— where n is 0, 1 or 2, —O—, 5- or 6-membered monocyclic rings and optional pendant functional groups, for example sulfo, hydroxy and carboxy. The moiety formed by a linker bonded to a reporter moiety may be designated -L-$R_x$. The reporter moiety may be reacted with a substance reactive therewith, whereby the linker becomes bonded to a conjugated substance; in this case, the linker typically contains a residue of a reactive group (e.g., the carbonyl group of an ester).

In certain embodiments, imaging agents include ethylenediamine. In certain aspectes, a valent metal ion is attached or coupled to ethylenediamine or a beta-adrenergic receptor/ethylenediamine conjugate. Any valent metal ion is contemplated for chelation to the agents of the present invention. For example, the valent metal ion includes, but is not limited to, Gd, Fe, Tc-99m, Cu-60, Cu-61, Cu-62, Cu-64, Cu-67, In-111, Tl-201, Ga-67, Ga-68, As-72, Re-186, Re-188, Ho-166, Y-90, Sm-153, Sr-89, In-212, or Bi-213. The valent metal ion may also be a therapeutic metal selected from the group consisting of arsenic, cobolt, copper, selenium, thallium and platinum. Thus the targeting properties of an imaging agent can be used to target therapies as well.

The inventors have found that some of these agents can be used in imaging methods using one or sometimes more than one imaging modality. For example, imaging an agent can combine the dynamic imaging capabilities of standard CT (or MRI) imaging agents with PET (or SPECT) imaging agents. For example, the agents set forth herein can be applied in a wide variety of combinations of imaging modalities, including PET, CT, SPECT, MRI, PET/CT, SPECT/CT, PET/MRI, SPECT/MRI, and/or optical imaging/MRI and various other combinations.

In certain embodiments, these agents may further comprise an imaging moiety that include any agent that is known or of use in imaging studies. An imaging moiety includes an agent that can be applied in the imaging of a cell or tissue, such as a myocardial tissue in a subject. Imaging by any modality known to those of ordinary skill in the art is contemplated under this definition of imaging moiety. In certain embodiments, the imaging moiety is a contrast media, such as a CT contrast media, an MRI contrast media, and optical contrast media, and an ultrasound contrast media. Contrast can either be positive or negative. Positive contrast media has a higher attenuation density than the surrounding tissue. This means that the contrast looks more opaque than the surrounding tissue when imaged. Negative contrast media has a lower attenuation density than the surrounding tissue. This means that the contrast looks less opaque than the body. Negative contrast is only found as a gas. Positive contrast is a substance with a high atomic number, but is also non-toxic. Contrast can be used to produce images of almost any hollow structure in the body.

Types of Positive Contrast Medium include Iodine based and non-Iodine based contrast media. Iodine based contrast media such as urografin or Omnipaque is used most commonly in radiology, due to its relatively harmless interaction with the body. It is primarily used to visualise vessels, but can also be used for tests of the urinary tract, uterus and fallopian tubes. Commonly used iodinated contrast agents include, but is not limited to diatrizoate, metrizoate, ioxaglate, iopamidol, iohexol, ioxilan, iopromide, and iodixanol. Non Iodine based contrast media includes, but is not limited to various forms of barium sulfate. Barium is mainly used in the imaging of the digestion system. Other contrast media include gadolinium for use in magnetic resonance imaging as a contrast agent. Types of Negative Contrast media include gases, usually air, carbon dioxide, or oxygen.

Any CT contrast media is contemplated for inclusion in the agents of the present invention. For example, the CT contrast media may be iothalamate, iohexol, diatrizoate, iopamidol, ethiodol, and iopanoate. In certain particular embodiments, the CT contrast media is diatrizoate.

MRI contrast media contemplated may be selected from the group consisting of a gadolinium chelate, a manganese chelate, a chromium chelate, and iron particles.

Optical contrast media can also be employed in the agents of the present invention. For example, optical contrast media can be fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, or dapoxyl dye.

Any ultrasound contrast media known to those of ordinary skill in the art is contemplated for inclusion in the agents of the present invention. For example, the ultrasound contrast media may be a perfluorinated agent, such as perfluorine or an analog of perfluorine. Any perfluorinated agent that is of use as an ultrasound contrast media is contemplated for inclusion in the present agents.

Additional embodiments of the present invention generally pertain to methods of imaging, typically of a subject, using a first imaging modality and/or a second imaging modality, that include: (a) administering to the subject a composition comprising a diagnostically effective or imageable amount of an agent, and (b) imaging using a first imaging modality by detecting a first signal from the agent; and alternatively or in addition (c) imaging using a second imaging modality by detecting a second signal from the agent, wherein the first imaging modality and the second imaging modality are performed either concurrently or consecutively. In certain embodiments, the two imaging modalities are the same or similar. Any imaging modality known to those of ordinary skill in the art is contemplated as an imaging modality to be applied in the present methods. For example, the imaging modalities can include PET, CT, SPECT, MRI, optical imaging, and/or ultrasound. Any combination of imaging modalities is contemplated for inclusion in the methods of the present invention. For example, the first and second imaging modalities can be PET and CT, SPECT and CT, PET and MRI, SPECT and CT, PET and MRI, SPECT and MRI, optical imaging and MRI, or PET and ultrasound, or SPECT and ultrasound. The subject may have a cardiovascular disease or may be in need of beta-blocker or similar therapy.

Other embodiments of the present invention generally pertain to methods of treating a subject with a cardiovascular disease, that include (a) obtaining a therapeutically effective amount of an agent described herein, and (b) administering to the subject a composition that includes a therapeutically effective amount of the agent. Any type of subject is contemplated for inclusion in these methods, including small mammals and humans. In certain embodiments, the subject is a human with a cardiovascular disease. The cardiovascular disease can be any type of cardiovascular diseases, such as, for example, hypertension, cardiopathy, myocardial disease, coronary artery disease, cardiac arrhythmia, congestive heart failure, atrial tachycardia, atrial fibrillation, atrial arrhythmia, ventricular fibrillation, ventricular arrhythmia, premature ventricular heartbeats, ventricular tachycardia, premature ventricular extrasystoles, atrioventricular dissociation, multifocal ectopic beats, bigeminal rhythm, trigeminal rhythm, angina pectoris, coronary insufficiency, sympathetically induced pain, or coronary spasm. In particular, the cardiovascular disease may be hypertension.

Additional embodiments of the present invention pertain to kits for preparing and/or using a diagnostic or therapeutic composition that comprises a sealed container including a predetermined quantity of an agent in accordance with any of the agents set forth above. In certain embodiments, the kit further includes a radionuclide. Any radionuclide known to those of ordinary skill in the art to be suitable for imaging can be included in the kits of the present invention. For example, the radionuclide can be Tc-99m, Cu-60, Cu-61, Cu-62, Cu-67, In-111, Tl-201, Ga-67, Ga-68, As-72, Re-188, Ho-166, Y-90, Sm-153, Sr-89, Gd-157, Bi-212, and/or Bi-213. The kit may include additional components beyond those set forth herein. The kit may be a kit for preparing a composition suitable for imaging, for chemotherapy, and/or for chemotherapy and radiation therapy.

The kit or the agent set forth above used in imaging of a subject in need of a beta-blocker therapy may also be applied to predict the efficacy of a beta-blocker therapy for the subject.

The imaging method using the agent or the kit set forth above may be also applied to select subjects by predicting a favorable response to a beta-blocker therapy. The subject may be a human in need of a beta-blocker therapy, such as a patient having a myocardial disease. A favorable response is typically indicated by an increased ratio of image density between heart and muscle, for example, at least 2, 3, 4, 5, 6 (or any number or range there between) fold higher than that between heart and another tissue, such as lung, liver, stomach, kidney or tumor, in the same subject.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and/or advantages of the present invention will become apparent from the following detailed description. It should be understood that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
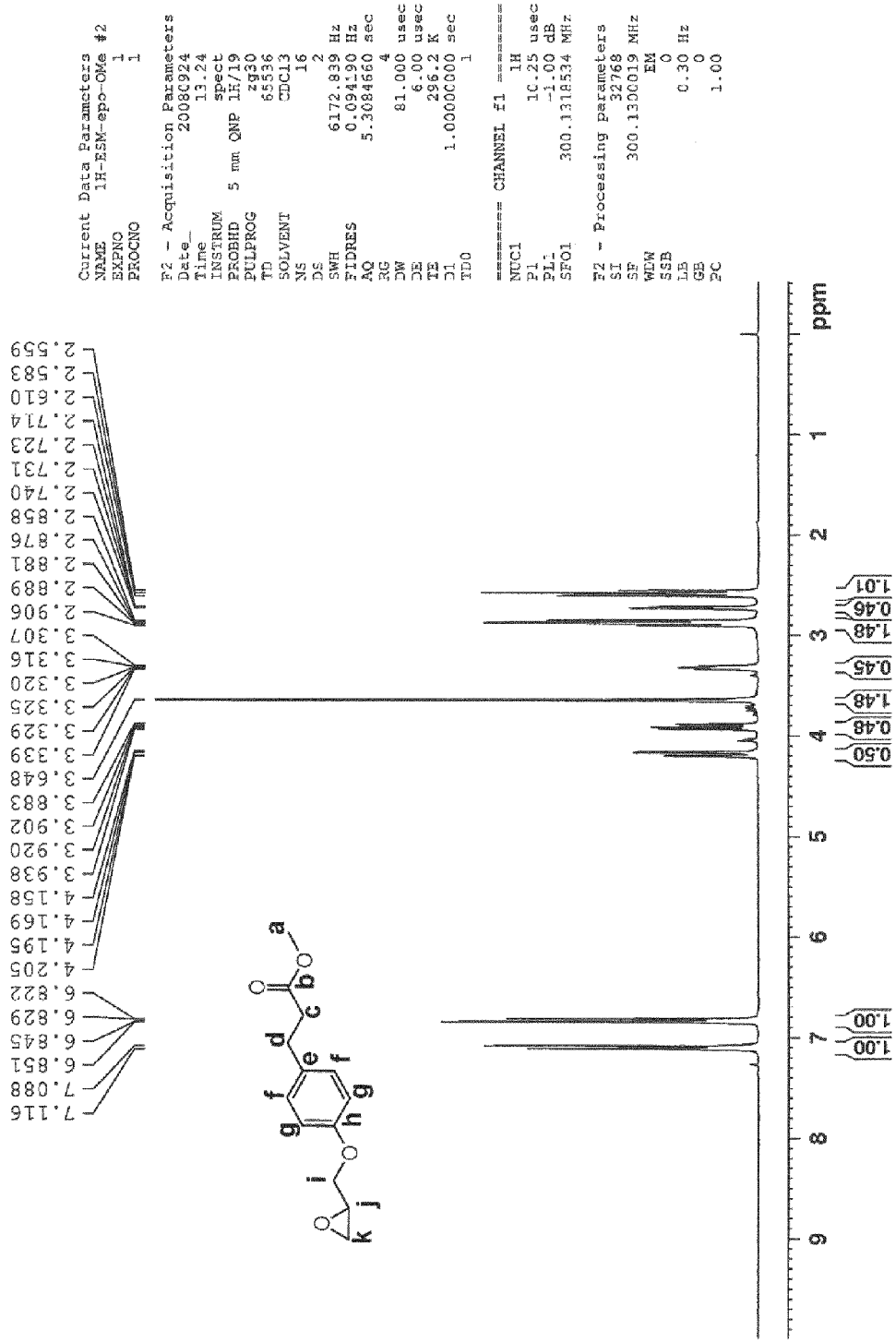
FIG. 1. $^1$H-NMR of 4-(oxiranylmethoxy)-benzenepropanoate methyl ester.

In certain embodiments, the present invention overcomes deficiencies in the art by providing novel EDA conjugates designed to target cardiovascular diseases or the heart. The EDA conjugates can be radiolabeled to be used to for diagnostics or imaging of subject. Further, the radiolabeled EDA conjugates comprising a beta-1 blocker can be used to predict the efficacy or assess the effectiveness of beta-1 blocker therapy. More particularly, the present invention provides the radiolabeled $^{99}$mTc-EDA conjugates to target cardiovascular diseases in a subject. Methods for treating a subject having a cardiovascular disease using the EDA conjugate comprising a beta-1 blocker are also provided.

I. Cardiovascular Disease

Congestive heart failure (CHF) affects nearly 5 million Americans with over 500,000 new cases diagnosed annually. By definition, CHF is a clinical syndrome in which heart disease reduces cardiac output, increases venous pressures, and is accompanied by molecular abnormalities that cause progressive deterioration of the failing heart (From; Heart Failure: Pathophysiology, Molecular Biology, and Clinical Management, Katz, A M, Lippincott Williams and Wilkins, 2000). Despite decades of research a detailed understanding of the causes of CHF are still unclear. However, scientific and clinical findings clearly demonstrate that an early phase of the disease process consists of a maladaptive response of the myocardium to stress known as 'cardiac hypertrophy' (also, 'hypertrophic cardiomyopathy'). Chronic overload on the heart in the setting of unremitting hypertension, valve disease, or tissue damage (myocardial infarction) results in a hypertrophic growth response which is initially adaptive in so far as cardiac output is temporarily restored but gradually becomes maladaptive over time resulting in decreased contractile function, cardiac dilatation and failure. Because the 5-year survival rate, once heart failure becomes symptomatic, is less that 50%, any definition of heart failure that does not consider the molecular processes that accelerate myocardial hypertrophy overlooks a major clinical feature of this syndrome.

Cardiovascular diseases are as varied as they are common, and can include without limitation, congestive heart failure, congestive cardiomyopathy, heart hypertrophy, left ventricular hypertrophy, right ventricular hypertrophy, post-infarction heart rupture, ventricular septal rupture, endocarditis (including bacterial), heart aneurysm, pulmonary heart disease, rheumatic heart disease, and ventricular dysfunction. Cardiovascular disease also encompasses cardiac valve disease, which includes but is not limited to aortic valve insufficiency, aortic valve stenosis, aortic valve prolapse, mitral valve prolapse, tricuspid valve prolapse, mitral valve insufficiency, mitral valve stenosis, and tricuspid valve stenosis. Cardiovascular disease further encompasses myocardial disease, which includes but is not limited to hypertrophic cardiomyopathy, congestive cardiomyopathy, aortic subvalvular stenosis, pulmonary subvalvular stenosis, restrictive cardiomyopathy, and Chagas cardiomyopathy. In other embodiments, a therapeutically effective dose refers to that amount of a modulator sufficient to result in prevention or amelioration of symptoms or physiological status of a hypertrophic cardiomyopathy resulting from a disorder selected from the group consisting of post-myocardial infarction remodeling, cardiac valve disease, sustained cardiac afterload, myocarditis, and familial hypertrophic cardiomyopathy. Cardiovascular disease can also encompass, without limitation, congenital heart defects such as aortic coarctation, aortopulmonary septal defect, trilogy of Fallot, ventricular heart septal defect, and familial hypertrophic cardiomyopathy.

II. Imaging

Biomedical imaging includes various modalities that are widely used by physicians and researchers to assist with not only the diagnosis of disease in a subject, but also to gain a greater understanding of normal structure and function of the body.

One such imaging modality that has been widely used is computerized tomography (CT). CT, developed in the 1970's, was the first imaging modality which marked a substantial improvement in medical imaging technology. By taking a series of X-rays, sometimes more than a thousand, from various angles and then combining them with a computer, CT made it possible to build up a three-dimensional image of any part of the body. Physicians could then instruct the computer to display two-dimensional slices from any angle and at any depth. In CT, intravenous injection of a radiopaque contrast agent can assist in identifying a suspected soft tissue mass when initial CT scans are not diagnostic. Similarly, contrast agents aid in assessing the vascularity of a soft tissue or bone lesion. For example, the use of contrast agents may allow delineation of the relationship of a tumor and adjacent vascular structures.

In the early 1980s, CT was joined by magnetic resonance imaging (MRI), a clinical diagnostic and research procedure that uses a high-strength magnet and radio-frequency signals to produce images, typically using characteristics of water molecules. The most abundant molecular species in biological tissues is water. It is the quantum mechanical "spin" of the water proton nuclei that ultimately gives rise to the signal in imaging experiments. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image, like a CT image, is normally displayed in two-dimensional slices.

Contrast agents used in MR imaging differ from those used in other imaging techniques. Their purpose is to aid in distinguishing between tissue components with identical signal characteristics and to shorten the relaxation times (which will produce a stronger signal on T1-weighted spin-echo MR images and a less intense signal on T2-weighted images. Examples of MRI contrast agents include gadolinium chelates, manganese chelates, chromium chelates, and iron particles. Although CT and MRI are useful in providing anatomical localization of lesions, the contrast media for these imaging modalities does not provide cellular target information.

Imaging modalities that provide information pertaining to information at the cellular level, such as cellular viability, include positron emission tomography (PET) and single-photon emission computed tomography (SPECT). In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high. Closely related to PET is single-photon emission computed tomography, or SPECT. The major difference between the two is that instead of a positron-emitting substance, SPECT uses a radioactive tracer that emits high-energy photons. SPECT is valuable for diagnosing coronary artery disease, and already some 2.5 million SPECT heart studies are done in the United States each year.

Optical imaging is another imaging modality that has gained widespread acceptance in particular areas of medicine. Examples include fluorescein angiography and indocyanine green angiography.

Another biomedical imaging modality that has gained widespread acceptance is ultrasound. Ultrasound imaging is used noninvasively to provide real-time cross-sectional and even three-dimensional images of soft tissue structures and blood flow information in the body. High-frequency sound waves and a computer are used to create images of blood vessels, tissues, and organs.

Ultrasound imaging of blood flow can be limited by a number of factors such as size and depth of the blood vessel. Ultrasonic contrast agents, a relatively recent development, include perfluorinated contrast agents, which are designed to overcome these limitations by helping to enhance grey-scale images and Doppler signals (Deng and Lizzi, 2002; Ophir and Parker, 1989; Goldberg et al., 1994; Goldberg, 1997; Forsberg, 1997).

The combination of more than one imaging modality can allow for the simultaneous acquisition of anatomical information and cellular information, thus allowing for improved resolution of a lesion of interest. Therefore, agents can be of particular value in the imaging of tumors. Furthermore, these agents also have the potential to reduce cost and lessen patient inconvenience. The patient would avoid the need to be injected twice. There may be cost savings to the patient because a single study using a imaging agent may be less expensive than two separate studies. Furthermore, the patient would save time because it would be expected that two studies using an imaging agent would take less time than two separate imaging studies using two different imaging agents.

Therefore, there is a need for an imaging agent that can be applied in the performance of more than one imaging modality. Description of any agent for use in imaging is very limited. See, e.g., U.S. Pat. No. 6,521,209 describing certain optically active magnetic resonance imaging agents, U.S. Pat. No. 6,770,259 pertaining to certain compositions that comprise a radiolabeled LTB4 binding agent and a radiolabeled perfusion imaging agent, and WO 2004/026344, describing agents that include a fluorescent dye and an MRI contrast agent. Thus, there is a need for novel imaging agents that can be used in concurrent imaging using more than one imaging modality.

Furthermore, in view of the epidemiological significance of cardiovascular diseases, there is the need for improved diagnostics and treatments. Cardiologists seek to identify coronary artery disease early in the disease progression in order to minimize the risk of heart attack. In early coronary artery disease, the coronary artery is only partially blocked, so there may be little or no wall motion abnormality, but there could be a perfusion abnormality. Though there were 2.8 million stress echo procedures (echocardiography) conducted in the United States in 2006, cardiac ultrasound is often inadequate for a definitive assessment of coronary artery disease. For instance, the motion of the heart wall can be difficult to see under stress conditions, particularly in obese patients. In addition, cardiac ultrasound without the use of a contrast agent cannot detect myocardial perfusion.

Currently, there is no ultrasound contrast agent approved by the FDA for use in cardiac ultrasound or myocardial perfusion imaging. Ultrasound contrast agents have been approved by the FDA for other non-perfusion indications in patients with suboptimal images, such as endocardial border delineation, in which ultrasound is used to view the boarders of ventricular chambers, and left ventricular opacification. Thus, ultrasound is used to view blood volume in the left ventricular chamber of the heart. In nuclear imaging, sestaM1B1 and thallium stress scans by SPECT are used to determine cardiac blood flow, not for myocardial cellular uptake. Though F-18 fluorodeoxyglucose by PET could assess glucose utilization of heart, but it does not provide therapeutic information.

III. Imaging Modalities and Imaging Agents

Certain embodiments of the present invention pertain to methods of imaging a subject using a first imaging modality and a second imaging modality following administration of a composition comprising one of the conjugates set forth herein. Any imaging modality known to those of ordinary skill in the art is contemplated by the present invention. Examples of imaging modalities are set forth as follows.

A. Examples of Imaging Modalities

Certain embodiments of the present invention pertain to methods of imaging a subject using a first imaging modality and a second imaging modality that involve administering to the subject a composition comprising a diagnostically effect amount of one of the agents of the present invention. Any imaging modality known to those of ordinary skill in the art is contemplated by the present invention. For example, in certain embodiments, the first imaging modality and the second imaging modality are selected from the group that includes PET, CT, SPECT, MRI, optical imaging, and ultrasound. Other examples of imaging modalities include digital subtraction angiography and x-ray angiography.

1. Computerized Tomography (CT)

Computerized tomography (CT) is contemplated as an imaging modality in the context of the present invention. By taking a series of X-rays, sometimes more than a thousand, from various angles and then combining them with a computer, CT made it possible to build up a three-dimensional image of any part of the body. A computer is programmed to display two-dimensional slices from any angle and at any depth.

In CT, intravenous injection of a radiopaque contrast agent can assist in the identification and delineation of soft tissue masses when initial CT scans are not diagnostic. Similarly, contrast agents aid in assessing the vascularity of a soft tissue or bone lesion. For example, the use of contrast agents may aid the delineation of the relationship of a tumor and adjacent vascular structures.

CT contrast agents include, for example, iodinated contrast media. Examples of these agents include iothalamate, iohexol, diatrizoate, iopamidol, ethiodol, and iopanoate. Gadolinium agents have also been reported to be of use as a CT contrast agent (see, e.g., Henson et al., 2004). For example, gadopentate agents has been used as a CT contrast agent (discussed in Strunk and Schild, 2004).

2. Magnetic Resonance Imaging (MRI)

Magnetic resonance imaging (MRI) is an imaging modality that is newer than CT that uses a high-strength magnet and radio-frequency signals to produce images. The most abundant molecular species in biological tissues is water. It is the quantum mechanical "spin" of the water proton nuclei that ultimately gives rise to the signal in imaging experiments. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT image, is normally displayed in two-dimensional slices.

Contrast agents used in MR imaging differ from those used in other imaging techniques. Their purpose is to aid in distinguishing between tissue components with identical signal characteristics and to shorten the relaxation times (which will produce a stronger signal on Ti-weighted spin-echo MR images and a less intense signal on T2-weighted images). Examples of MRI contrast agents include gadolinium chelates, manganese chelates, chromium chelates, and iron particles.

Both CT and MRI provide anatomical information that aid in distinguishing tissue boundaries and vascular structure. Compared to CT, the disadvantages of MRI include lower patient tolerance, contraindications in pacemakers and certain other implanted metallic devices, and artifacts related to multiple causes, not the least of which is motion (Alberico et al., 2004). CT, on the other hand, is fast, well tolerated, and readily available but has lower contrast resolution than MRI and requires iodinated contrast and ionizing radiation (Alberico et al., 2004). A disadvantage of both CT and MRI is that neither imaging modality provides functional information at the cellular level. For example, neither modality provides information regarding cellular viability.

3. PET and SPECT

Imaging modalities that provide information pertaining to information at the cellular level, such as cellular viability, include positron emission tomography (PET) and single-photon emission computed tomography (SPECT). In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high.

Closely related to PET is single-photon emission computed tomography, or SPECT. The major difference between the two is that instead of a positron-emitting substance, SPECT uses a radioactive tracer that emits high-energy photons. SPECT is valuable for diagnosing coronary artery disease, and already some 2.5 million SPECT heart studies are done in the United States each year.

PET radiopharmaceuticals for imaging are commonly labeled with positron-emitters such as $^{11}$C, $^{13}$N, $^{15}$O, $^{18}$F, $^{82}$Rb, $^{62}$Cu, and $^{68}$Ga. SPECT radiopharmaceuticals are commonly labeled with positron emitters such as $^{99m}$Tc, $^{201}$Tl, and $^{67}$Ga. Regarding brain imaging, PET and SPECT radiopharmaceuticals are classified according to blood-brain-barrier permeability, cerebral perfusion and metabolism receptor-binding, and antigen-antibody binding (Saha et al., 1994). The blood-brain-barrier SPECT agents, such as $^{99m}$TcO4-DTPA, $^{201}$Tl, and [$^{67}$Ga]citrate are excluded by normal brain cells, but enter into tumor cells because of altered BBB. SPECT perfusion agents such as [$^{123}$I]IMP, [$^{99m}$Tc]HMPAO, [$^{99m}$Tc]ECD are lipophilic agents, and therefore diffuse into the normal brain. Important receptor-binding SPECT radiopharmaceuticals include [$^{123}$I]QNE, [$^{123}$I]IBZM, and [$^{123}$I] iomazenil. These tracers bind to specific receptors, and are of importance in the evaluation of receptor-related diseases 4. Optical Imaging Optical imaging is another imaging modality that has gained widespread acceptance in particular areas of medicine. Examples include optical labeling of cellular components, and angiography such as fluorescein angiography and indocyanine green angiography. Examples of optical imaging agents include, for example, fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye.

5. Ultrasound

Another biomedical imaging modality that has gained widespread acceptance is ultrasound. Ultrasound imaging has been used noninvasively to provide real-time cross-sectional and even three-dimensional images of soft tissue structures and blood flow information in the body. High-frequency sound waves and a computer to create images of blood vessels, tissues, and organs.

Ultrasound imaging of blood flow can be limited by a number of factors such as size and depth of the blood vessel. Ultrasonic contrast agents, a relatively recent development, include perfluorine and perfluorine analogs, which are designed to overcome these limitations by helping to enhance grey-scale images and Doppler signals.

B. Procedure for Imaging

For example, as set forth above, the imaging modality may include, but are not limited to, CT, MRI, PET, SPECT, ultrasound, or optical imaging. Other examples of imaging modalities known to those of ordinary skill in the art are contemplated by the present invention.

The imaging modalities are performed at any time during or after administration of the composition comprising the diagnostically effective amount of the agent that comprises a carbohydrate conjugated to two imaging moieties. For example, the imaging studies may be performed during administration of the imaging agent of the present invention, or at any time thereafter. In some embodiments, the first imaging modality is performed beginning concurrently with the administration of the imaging agent, or about 1 sec, 1 hour, 1 day, or any longer period of time following administration of the imaging agent, or at any time in between any of these stated times.

The second imaging modality may be performed concurrently with the first imaging modality, or at any time following the first imaging modality. For example, the second imaging modality may be performed about 1 sec, about 1 hour, about 1 day, or any longer period of time following completion of the first imaging modality, or at any time in between any of these stated times. In certain embodiments of the present invention, the first and second imaging modalities are performed concurrently such that they begin at the same time following administration of the One of ordinary skill in the art would be familiar with performance of the various imaging modalities contemplated by the present invention.

In some embodiments of the present methods of imaging, the same imaging device is used to perform a first imaging modality and a second imaging modality. For example, in certain embodiments, diagnostic agent (x-ray contrast media or optical contrast) and radio metallic substance are conjugated to the same carbohydrate. It may be employed for PET/CT, SPECT/CT, or optical/CT applications. For example, in certain embodiments, radioactive agent or optical contrast and non-radioactive metallic substance (gadolinium, iron, manganese) are conjugated to the same carbohydrate. It may be employed for PET/MRI, SPECT/MRI, or optical/MRI applications. For example, in certain embodiments, a therapeutic agent and a radiotherapeutic metallic substance are conjugated to the same carbohydrate. It may be employed for radio chemotherapy. In other embodiments, a different imaging device is used to perform the second imaging modality. One of ordinary skill in the art would be familiar with the imaging devices that are available for performance of a first imaging modality and a second imaging modality, and the skilled artisan would be familiar with use of these devices to generate images.

IV. Radiopharmaceuticals and Radioimaging

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

V. Cardiotheranostics

The combination of a diagnostic test with a therapeutic entity is termed theranostics. The term applied to cardiac imaging and therapy generally refers to a diagnostic test which is designed to distinguish patients who will likely benefit from a specific cardiotherapeutic intervention from patients who are either unlikely to respond to a treatment or likely to manifest significant side-effects. With many areas of disease research focused on developing molecularly targeted therapies, imaging procedures that can be coupled to these specific therapies are important technological advances. The concepts underlying the theranostic strategy are particularly applicable in approaches to cardiovascular diseases, since imaging procedures are such a critical diagnostic element of clinical practice in treating these diseases, and the identification of their associated molecular targets is well underway.

A number of therapeutic targets have been correlated with cardiovascular disease processes and may be advantageously coupled to an imaging procedure as a theranostic, including without limitation, receptors for adenosine, angiotensin, thromboxane, endothelin, the glycoprotein GPIIb/IIIa, and catecholamines. Of particular interest are the catecholamine, or adrenergic, receptors of the cardiac sympathetic system which plays an important role in the regulation of left ventricular function and the pathophysiology of left ventricular dysfunction.

Adrenergic receptors are G-protein coupled receptors of two main types, $\alpha$ and $\beta$, each with subtypes which are expressed in a variety of tissues and are implicated in cardiovascular disease. When bound by specific catecholamines, both types of adrenergic receptors initiate signaling cascades which mediate sympathetic responses (fight-or-flight responses). The a-adrenergic receptors have the subtypes $\alpha_1$, which is $G_q$ coupled, and $\alpha_2$ which is $G_i$ coupled. The $\beta$-adrenergic receptors have the subtypes $\beta_1$, $\beta_2$ and $\beta_3$, all coupled to $G_s$ proteins, which in turn are linked to adenylyl cyclase. As part of a cardiotheranostic approach contemplated for a cardiovascular disease such as a cardiomyopathy, for instance, targeting an adrenergic receptor can have the advantage of being able to directly target the myocardium with imaging agents while choosing an adrenergic targeting moiety from the wide variety of available, well-characterized adrenergic antagonists (i.e. alpha and beta blockers).

Compounds useful for targeting beta-adrenergic receptors can include beta blockers or $\beta$-blockers, which are a class of drugs used for various indications, but particularly for the management of cardiac arrhythmias and cardioprotection after myocardial infarction. Beta blockers block the action of endogenous catecholamines (epinephrine (adrenaline) and norepinephrine (noradrenaline) in particular), on $\beta$-adrenergic receptors. The advantages of blocking beta-adrenergic receptors are generally dictated by the disease process and tissues involved, since the beta subtypes are somewhat tissue-specific in their expression. $\beta$1-Adrenergic receptors are located mainly in the heart and in the kidneys. $\beta$2-Adrenergic receptors are located mainly in the lungs, gastrointestinal tract, liver, uterus, vascular smooth muscle, and skeletal muscle. β3-receptors are located in fat cells. Beta blockers may also be referred to as beta-adrenergic blocking agents, beta-adrenergic antagonists, or beta antagonists. Some β-1 receptor agents such as practolol, metoprolol, atenolol, acebutolol, celiprolol, esmolol, betaxolol, bevantolol and bisoprolol have shown the selectivity in myocardial diseases. Contemplated in particular embodiments is the modification of these and other agents for improved diagnostic and therapeutic applications.

VI. Ethylenediamine (EDA)

In particular embodiments, the present invention utilizes ethylenediamine (EDA) conjugates as a labeling agent for targeting heart or heart muscles, as well as for the assessment of a pharmaceutical agent's effectiveness on treating of cardiovascular diseases, or for treating a cardiovascular disease such as hypertension.

Ethylenediamine is an organic compound with the formula $C_2H_4(NH_2)_2$. This colorless liquid with an ammonia-like odor is a strongly basic amine. It is a widely used building block in chemical synthesis, with approximately 500,000,000 kg being produced in 1998. The chemical structure is shown below.

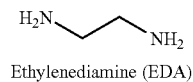

Ethylenediamine (EDA)

The advantage of conjugating the EDA with tissue targeting ligands is that the specific binding properties of the tissue targeting ligand concentrates the radioactive signal over the area of interest. It is envisioned that the use of EDA as a labeling strategy can be effective with ligands designed for targeting disease receptors, such as beta receptor.

Ethylenediamine is manufactured by reacting ammonia and 1,2-dichloroethane as known to ordinary people skilled in the art. The reaction yields the mixture of ethylenediamine and the linear polyamines. Ethylenediamine is used in large quantities for production of many industrial chemicals. It forms derivatives with carboxylic acids (including fatty acids), nitrites, alcohols (at elevated temperatures), alkylating agents, carbon disulfide, and aldehydes and ketones. Because of its bifunctional nature, having two amines, it readily forms heterocycles such as imidazolidines.

Ethylenediamine has been used as chelating agents or precursors thereof. The most prominent derivative of ethylenediamine is EDTA, which is derived from ethylenediamine via a Strecker synthesis involving cyanide and formaldehyde. Hydroxyethylethyelenediamine is another commercially significant chelating agent. The salen ligands, derived from the condensation of salicylaldehydes and ethylenediamine, are popular chelating agents in the research laboratory although not commercially significant.

Numerous bio-active compounds contain the N—$CH_2$—$CH_2$—N linkage, including aminophylline and some antihistamines. Salts of ethylenebisdithiocarbamate are commercially significant fungicides. Some imidazoline-containing fungicides are derived from ethylenediamine.

Ethylenediamine is the first member of the so-called polyethylene amines, other members being: Diethylenetriamine, abbreviated dien or DETA, ($H_2N$—$CH_2CH_2$—NH—$CH_2CH_2$—$NH_2$, an analog of diethylene glycol); Triethylenetetramine, abbreviated trien or TETA, ($H_2N$—$CH_2CH_2$—NH—$CH_2CH_2$—NH—$CH_2CH_2$—$NH_2$); Tetraethylenepentamine, abbreviated TEPA, ($H_2N$—$CH_2CH_2$—NH—$CH_2CH_2$—NH—$CH_2CH_2$—NH—$CH_2CH_2$—$NH_2$); Pentaethylenehexamine, abbreviated PEHA, ($H_2N$—$CH_2CH_2$—NH—$CH_2CH_2$—NH—$CH_2CH_2$—NH—$CH_2CH_2$—NH—$CH_2CH_2$—$NH_2$), up to polyethylene amine. Similarly piperazine is an analogue of dioxane.

In terms of quantities produced, ethylenediamine is the most significant diamine (aside from diaminohexane, which is a precursor to Nylon 66). Related derivatives of ethylenediamine include tetramethylethylenediamine, abbreviated (TMEDA), $(CH_3)_2N$—$CH_2CH_2$—$N(CH_3)_2$ and tetraethylethylenediamine, abbreviated (TEEDA), $(C_2H_5)_2N$—$CH_2CH_2$—$N(C_2H_5)_2$.

VII. Beta Blockers

In certain embodiments, the present invention utilizes agents comprising ethylenediamine (EDA) conjugated to or embedded in a beta-receptor targeting moeity, which may comprise a beat blocker. These agents can be used as diagnostic or therapeutic agents for cardiovascular diseases due to a binding specificity for beta-adrenergic receptors. As used herein, a "beta blocker therapy" refers to any therapy comprise using one or more beta blocker or derivatives thereof to treat a subject.

A beta blocker will, in general, have the opposite downstream effects as a beta-agonist. A natural beta-agonist such as epinephrine binds and stimulates beta receptors, while a beta blocker binding the same receptors suppresses their actions. Stimulation by epinephrine of β1 receptors increases cardiac conduction velocity and automaticity. Stimulation by epinephrine of β1 receptors on kidney cells causes release of the enzyme, renin, which is involved in regulating blood pressure. Stimulation of β2 receptors by epinephrine can induce smooth muscle relaxation, skeletal muscle tremor, and increases in liver and skeletal muscle glycogenolysis. Stimulation of beta receptors in adipose tissues induces lipolysis. Beta blockers inhibit these normal epinephrine-mediated sympathetic actions, but have minimal effect on resting subjects. That is, they reduce the effect of excitement and/or physical exertion on heart rate and force of contraction, dilation of blood vessels and opening of bronchi, and also reduce tremor and breakdown of lipids and glycogen.

Beta blockers (or β-blockers) as a class of drugs are indicated in the treatment of a variety of cardiovascular ailments including, without limitation, hypertension, angina, and arrythmia, and more particularly for the management of cardiac arrhythmias and cardioprotection after myocardial infarction. A particular example of a beta blocker is esmolol. Esmolol (Brevibloc™) is a cardioselective beta1 receptor blocker with rapid onset, a very short duration of action, and no significant intrinsic sympathomimetic or membrane stabilizing activity at therapeutic dosages. Esmolol decreases the force and rate of heart contractions by blocking beta-adrenergic receptors of the sympathetic nervous system, which are found in the heart and other organs of the body. Esmolol prevents the action of two naturally occurring substances: epinephrine and norepinephrine. In clinical applications, esmolol is often given by slow intravenous injection. It has been commonly used in patients during surgery to prevent or treat tachycardia, and has been also used in treatment of acute supraventricular tachycardia. Esmolol is also the drug of choice when aortic dissection is suspected.

The non-selective beta blockers have antihypertensive effects which appear to involve: reduction in cardiac output (due to negative chronotropic and inotropic effects), reduction in renin release from the kidneys, and suppression of sympathetic activity in the nervous system effect to reduce sympathetic activity (for those β-blockers that do cross the blood-brain barrier, e.g., Propranolol).

Antianginal effects of beta blockers, also, result from negative chronotropic and inotropic effects, decreasing cardiac workload and oxygen demand.

The antiarrhythmic effects of beta blockers arise from sympathetic nervous system blockade—resulting in depression of sinus node function and atrioventricular node conduction, and prolonged atrial refractory periods. Sotalol, in particular, has additional antiarrhythmic properties and prolongs action potential duration through potassium channel blockade.

Blockade of the sympathetic nervous system on renin release leads to reduced aldosterone via the renin angiotensin aldosterone system with a resultant decrease in blood pressure due to decreased sodium and water retention.

Some beta blockers (e.g., oxprenolol and pindolol) exhibit intrinsic sympathomimetic activity (ISA). These agents are capable of exerting low level agonist activity at the β-adrenergic receptor while simultaneously acting as a receptor site antagonist. These agents, therefore, may be useful in individuals exhibiting excessive bradycardia with sustained beta blocker therapy. Agents with ISA are not used in post-myocardial infarction as they have not been demonstrated to be beneficial. They may also be less effective than other beta blockers in the management of angina and tachyarrhythmia.

Although beta blockers were once contraindicated in congestive heart failure, as they have the potential to worsen the condition, studies in the late 1990s showed their positive effects on morbidity and mortality in congestive heart failure. Bisoprolol, carvedilol and sustained-release metoprolol are specifically indicated as adjuncts to standard ACE inhibitor and diuretic therapy in congestive heart failure. The beta blockers are a benefit due to the reduction of the heart rate which will lower the myocardial energy expenditure. This is turns prolongs the diastolic filling and lengthens coronary perfusion. Beta blockers have also been a benefit to improving the ejection fraction of the heart despite an initial reduction in it. Trials have shown that Beta blockers reduce the absolute risk of death by 4.5% over a 13 month period. As well as reducing the risk of mortality, the number of hospital visits and hospitalizations were also reduced in the trials.

VIII. Valent Metal Ions and Radionuclides

It is envisioned that the EDA-tissue specific ligand conjugates of the current invention may be chelated to any radionuclides and used for radionuclide therapy. Generally, it is believed that virtually any α, β-emitter, γ-emitter, or β, γ-emitter can be used in conjunction with the invention. Preferred α emitters include bismuth-213, astatine-211, and radium-223. Preferred β, γ-emitters include $^{166}$Ho, $^{188}$Re, $^{186}$Re, $^{153}$Sm, and $^{89}$Sr. Preferred β-emitters include $^{90}$Y and $^{225}$Ac. Preferred γ-emitters include $^{67}$Ga, $^{68}$Ga, $^{64}$Cu, $^{62}$Cu and $^{111}$In. Preferred α-emitters include $^{211}$At and $^{212}$Bi. It is also envisioned that para-magnetic substances, such as Gd, Mn, Cu or Fe can be chelated with EDA for use in conjunction with the present invention.

A variety of valent metal ions, or radionuclides, are known to be useful for radioimaging. Examples include $^{67}$Ga, $^{68}$Ga, $^{99m}$Tc, $^{111}$In, $^{123}$I, $^{125}$I, $^{131}$I, $^{169}$Yb, $^{60}$Cu, $^{61}$Cu, $^{62}$Cu, $^{201}$Tl, $^{72}$A, and $^{157}$Gd. Due to better imaging characteristics and lower price, attempts have been made to replace the $^{123}$I, $^{131}$I, $^{67}$Ga and $^{111}$In labeled compounds with corresponding $^{99m}$Tc labeled compounds when possible.

A number of factors must be considered for optimal radioimaging in humans. To maximize the efficiency of detection, a valent metal ion that emits gamma energy in the 100 to 200 keV range is preferred. A "gamma emitter" is herein defined as an agent that emits gamma energy of any range. One of ordinary skill in the art would be familiar with the various valent metal ions that are gamma emitters. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site. $^{99m}$Tc is a preferred radionuclide because it emits gamma radiation at 140 keV, it has a physical half-life of 6 hours, and it is readily available on-site using a molybdenum-99/technetium-99m generator. One of ordinary skill in the art would be familiar with methods to determine optimal radioimaging in humans.

In other embodiments of the agents of the present invention, including agents suitable for chemotherapy and radiation therapy, EDA may be chelated to a therapeutic radionuclide. For example, in some embodiments of the present invention, the therapeutic radionuclide is a beta-emitter. As herein defined, a beta emitter is any agent that emits beta energy of any range. Examples of beta emitters include Re-188, Re-186, Ho-166, Y-90, Bi-212, Bi-213, and Sn-153. The beta emitters may or may not also be gamma emitters. One of ordinary skill in the art would be familiar with the use of beta emitters in the treatment of cardiovascular disease.

In further embodiments of the agents of the present invention, the valent metal ion is a therapeutic metal ion that is not a beta emitter or a gamma emitter. For example, the therapeutic metal ion may be platinum, cobalt, copper, arsenic, selenium and thallium. Agents including these therapeutic metal ions may be applied in the methods of the present invention directed to the treatment of cardiovascular disease, such as the treatment of hypertension. Methods of performing chemotherapy and radiation therapy that involve the agents of the present invention are discussed in greater detail below.

IX. Imaging Moieties

In certain particular embodiments of the present invention, the agents of the present invention include an imaging moiety. Any imaging agent known to those of ordinary skill in the art is contemplated as an imaging moiety. A "moiety" is defined herein to be a part of a molecule. As defined herein, an "imaging moiety" is a part of a molecule that is a agent or compound that can be administered to a subject, contacted with a tissue, or applied to a cell for the purpose of facilitating visualization of particular characteristics or aspects of the subject, tissue, or cell through the use of an imaging modality. Any imaging agent known to those of ordinary skill in the art is contemplated as an imaging moiety of the present invention.

In certain embodiments, the imaging moiety is a contrast media. Examples include CT contrast media, MRI contrast media, optical contrast media, ultrasound contrast media, or any other contrast media to be used in any other form of imaging modality known to those of ordinary skill in the art. Particular specific examples of these contrast media are set forth above in the background section and summary of the invention, which is specifically incorporated into this section. Examples include diatrizoate (a CT contrast agent), a gadolinium chelate (an MRI contrast agent), and sodium fluorescein (an optical contrast media).

X. Radiolabeled Agents

Certain embodiments of the present invention pertain to methods of synthesizing a radiolabeled imaging agent for imaging and methods of synthesizing therapeutic agents for chemotherapy and radiation therapy. Other embodiments of the present invention pertain to kits for preparing these radiolabeled agents. Radiolabeled agents, compounds, and compositions provided by the present invention are provided having a suitable amount of radioactivity. For example, in forming $^{99m}$Tc radioactive complexes, it is generally preferred to form radioactive complexes in solutions containing radioactivity at concentrations of from about 0.01 millicurie (mCi) to about 300 mCi per mL.

The radiolabeled imaging agents provided by the present invention can be used for visualizing sites in a mammalian body. In accordance with this invention, the imaging agents are administered by any method known to those of ordinary skill in the art. For example, administration may be in a single unit injectable dose. Any of the common carriers known to those with skill in the art, such as sterile saline solution or plasma, may be utilized after radiolabeling for preparing the agents of the present invention for injection. Generally, a unit dose to be administered has a radioactivity of about 0.01 mCi to about 300 mCi, preferably 10 mCi to about 200 mCi. The solution to be injected at unit dosage is from about 0.01 mL to about 10 mL.

After intravenous administration of an agent of the present invention that is an imaging agent, imaging of the organ or tumor in vivo can take place, if desired, in hours or even longer, after the radiolabeled reagent is introduced into a patient. In most instances, a sufficient amount of the administered dose will accumulate in the area to be imaged within about 0.1 of an hour. As set forth above, imaging may be performed using any method known to those of ordinary skill in the art. Examples include PET, SPECT, and gamma scintigraphy. In gamma scintigraphy, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

XI. Drug Assessment

Certain drug-based EDA conjugates can be applied in measuring the pharmacological response of a subject to a drug. A wide range of parameters can be measured in determining the response of a subject to administration of a drug. One of ordinary skill in the art would be familiar with the types of responses that can be measured. These responses depend in part upon various factors, including the particular drug that is being evaluated, the particular disease or condition for which the subject is being treated, and characteristics of the subject.

XII. Pharmaceutical Preparations

Pharmaceutical compositions of the present invention comprise a therapeutically or diagnostically effective amount of an imaging agent or therapeutic agent of the claimed invention. The phrases "pharmaceutical or pharmacologically acceptable" or "therapeutically effective" or "diagnostically effective" refers to molecular entities and compositions that do not produce an adverse, allergic or other untoward reaction when administered to an animal, such as, for example, a human, as appropriate. The preparation of therapeutically effective or diagnostically effective compositions will be known to those of skill in the art in light of the present disclosure, as exemplified by Remington's Pharmaceutical Sciences, 21th Ed. Lippincott Williams & Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "a composition comprising a therapeutically effective amount" or "a composition comprising a diagnostically effective amount" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the present compositions is contemplated.

The compositions of the present invention may comprise different types of carriers depending on whether it is to be administered in solid, liquid or aerosol form, and whether it need to be sterile for such routes of administration as injection. The imaging agents and therapeutic agents of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art.

The actual required amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an imaging agent or an therapeutic agent. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight to about 1000 mg/kg/body weight or any amount within this range, or any amount greater than 1000 mg/kg/body weight per administration.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The imaging agents and therapeutic agents of the present invention may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, carbohydrates, sodium chloride or combinations thereof.

Sterile injectable solutions are prepared by incorporating the radiolabeled ethylenediamine derivative in the required amount of the appropriate solvent with various amounts of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

XIII. Kits

Certain embodiments of the present invention are generally concerned with kits for preparing a composition comprising a radiolabeled imaging agent for imaging or kits for preparing a composition comprising a radiolabeled agent for chemotherapy and radiation therapy. A kit can include a sealed vial containing a predetermined quantity of a agent of the present invention, and optionally a sufficient amount of reducing agent to label the agent with a radionuclide. In some embodiments of the present invention, the kit includes a radionuclide. In particular embodiments, the specific radionuclide is $^{99m}$Tc.

The kit may also contain conventional pharmaceutical adjunct materials such as, for example, pharmaceutically acceptable salts to adjust the osmotic pressure, buffers, preservatives, antioxidants, and the like.

In certain embodiments, an antioxidant and a transition chelator are included in the composition to prevent oxidation of the chelator moiety. In certain embodiments, the antioxidant is vitamin C (ascorbic acid). However, it is contemplated that any other antioxidant known to those of ordinary skill in the art, such as tocopherol, pyridoxine, thiamine, or rutin, may also be used. The components of the kit may be in liquid, frozen or dry form. In a preferred embodiment, kit components are provided in lyophilized form.

When reagents and/or components comprising a kit are provided in a lyophilized form (lyophilisate) or as a dry powder, the lyophilisate or powder can be reconstituted by the addition of a suitable solvent. In particular embodiments, the solvent may be a sterile, pharmaceutically acceptable buffer and/or other diluent. It is envisioned that the solvent may also be provided as part of a kit.

When the components of a kit are provided in one and/or more liquid solutions, the liquid solution may be, by way of non-limiting example, a sterile, aqueous solution. The compositions may also be formulated into a syringeable composition. In this case, the container means may itself be a syringe, pipette, and/or other such like apparatus, from which the formulation may be applied to an infected area of the body, injected into an animal, and/or even applied to and/or mixed with the other components of the kit.

XIV. Disease

Certain aspects of the present invention are generally concerned with methods of treating cardiovascular disease in a subject using an agent of the present invention or use imaging by the agents of the present invention to select subjects more susceptible to therapy. Cardiovascular disease refers to the class of diseases that involve the heart or blood vessels (arteries and veins). While the term technically refers to any disease that affects the cardiovascular system, it is often used to refer to those related to atherosclerosis (arterial disease). These conditions have similar causes, mechanisms, and treatments.

Most Western countries face high and increasing rates of cardiovascular disease. Each year, heart disease kills more Americans than cancer. Diseases of the heart alone caused 30% of all deaths, with other diseases of the cardiovascular system causing substantial further death and disability. Up until the year 2005, it was the number 1 cause of death and disability in the United States and most European countries. A large histological study (PDAY) showed vascular injury accumulates from adolescence, making primary prevention efforts necessary from childhood.

By the time that heart problems are detected, the underlying cause (atherosclerosis) is usually quite advanced, having progressed for decades. There is therefore increased emphasis on preventing atherosclerosis by modifying risk factors, such as healthy eating, exercise and avoidance of smoking.

The cardiovascular disease can be any type of cardiovascular diseases, such as, for example, hypertension, cardiopathy, myocardial disease, coronary artery disease, cardiac arrhythmia, congestive heart failure, atrial tachycardia, atrial fibrillation, atrial arrhythmia, ventricular fibrillation, ventricular arrhythmia, premature ventricular heartbeats, ventricular tachycardia, premature ventricular extrasystoles, atrioventricular dissociation, multifocal ectopic beats, bigeminal rhythm, trigeminal rhythm, angina pectoris, coronary insufficiency, sympathetically induced pain, or coronary spasm. In certain aspects the cardiovascular disease may be hypertenstion.

Disease or disorder of myocardium is condition in which there is a deviation from or interruption of the normal structure or function of the myocardium, the middle and thickest layer of the heart wall, composed of heart muscle. Disease of the myocardium can also be considered to be ischemic (poor blood supply to the heart muscle) or nonischemic, implying disease within the heart muscle itself. Ischemic myocardial disease is well described and is amenable to vessel bypass, stents, applied growth factors and many other interventions. Diabetes is perhaps the best known physiologic model for accelerated ischemic disease of the myocardium. Nonischemic myocardial disease (see also nonischemic cardiomyopathy) is an entirely different entity in myocardial disease. Chagasic heart failure (see also Carlos Chagas) is perhaps the best known physiologic model in myocardial autonomic insufficiency.

Myocardial infarction (heart attack) is a serious result of coronary artery disease. Coronary artery disease occurs from atherosclerosis, when arteries become narrow or hardened due to cholesterol plaque build-up. Further narrowing may occur from thrombi (blood clots) that form on the surfaces of plaques. Myocardial infarction occurs when a coronary artery is so severely blocked that there is a significant reduction or break in the blood supply, causing damage or death to a portion of the myocardium (heart muscle). Depending on the extent of the heart muscle damage, the patient may experience significant disability or die as a result of myocardial infarction

XV. Chemotherapy and Radiation Therapy ("Radiochemotherapy")

Certain embodiments of the present invention pertain to methods of treating a subject with a cardiovascular disease that involve administering to the subject a composition comprising a therapeutically effective amount of an agent or composition of the present invention comprising an EDA-conjugate of a beta-receptor targeting compound.

One of ordinary skill in the art would be familiar with the design of chemotherapeutic protocols and radiation therapy protocols that can applied in the administration of the agents of the present invention. As set forth below, these agents may be used in combination with other therapeutic modalities directed at treatment of an cardiovascular disease, such as myocardial disease or hypertension. Furthermore, one of ordinary skill in the art would be familiar with selecting an appropriate dose for administration to the subject. The protocol may involve a single dose, or multiple doses. The patient would be monitored for toxicity and response to treatment using protocols familiar to those of ordinary skill in the art.

As used herein the term "radionuclide" is defined as a radioactive nuclide (a species of atom able to exist for a measurable lifetime and distinguished by its charge, mass, number, and quantum state of the nucleus) which, in specific embodiments, disintegrates with emission of corpuscular or electromagnetic radiation. The term may be used interchangeably with the term "radioisotope".

The term "drug" as used herein is defined as a compound which aids in the treatment of disease or medical condition or which controls or improves any physiological or pathological condition associated with the disease or medical condition. In a specific embodiment, the drug is a EDA conjugated to a beta-blocker.

As used herein the specification, "a" or "an" may mean one or more. As used herein in the claim(s), when used in conjunction with the word "comprising", the words "a" or "an" may mean one or more than one. As used herein "another" may mean at least a second or more. The term "moiety" as used herein refers to a part of the agent or compound of the present invention.

EXAMPLES

The following examples are included to demonstrate preferred embodiments of the invention. It should be appreciated by those of skill in the art that the techniques disclosed in the examples that follow represent techniques identified by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Ethylenediamine-esmolol (EDA-ESM)

EDA-ESM was synthesized in a three-step manner. Step 1 and Step 2 are modifications of the procedures of U.S. Pat. No. 4,387,103; Erhardt et al., 1982; Ronda et al., 1995, each of which is incorporated herein by reference in its entirety. For instance, in step 1, sodium metal was used instead of sodium carbonate to eliminate pressure reactor. Chemicals were purchased from Aldrich Chemical Company (Milwaukee, Wis.). Synthesis scheme of EDA-ESM is shown below.

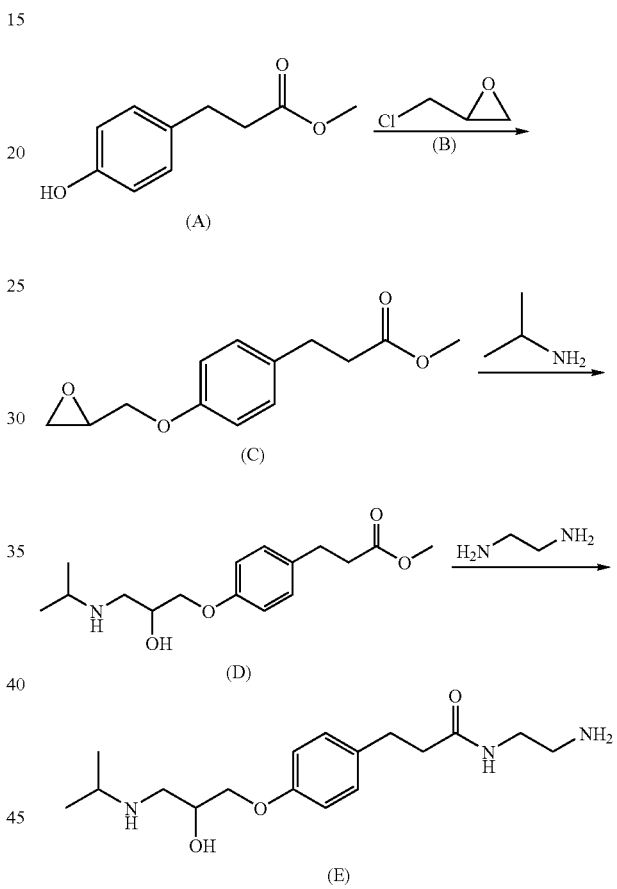

Step 1: Synthesis of 4-(oxiranylmethoxy)-benzenepropanoate methyl ester

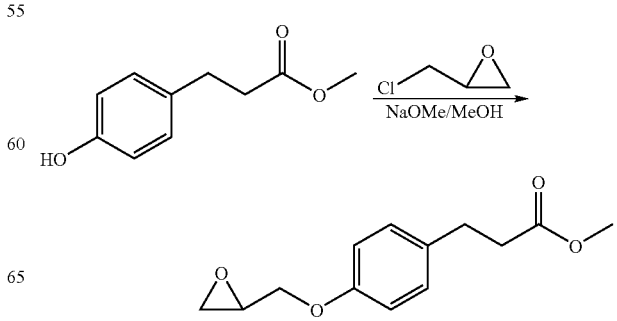

Figure 2:
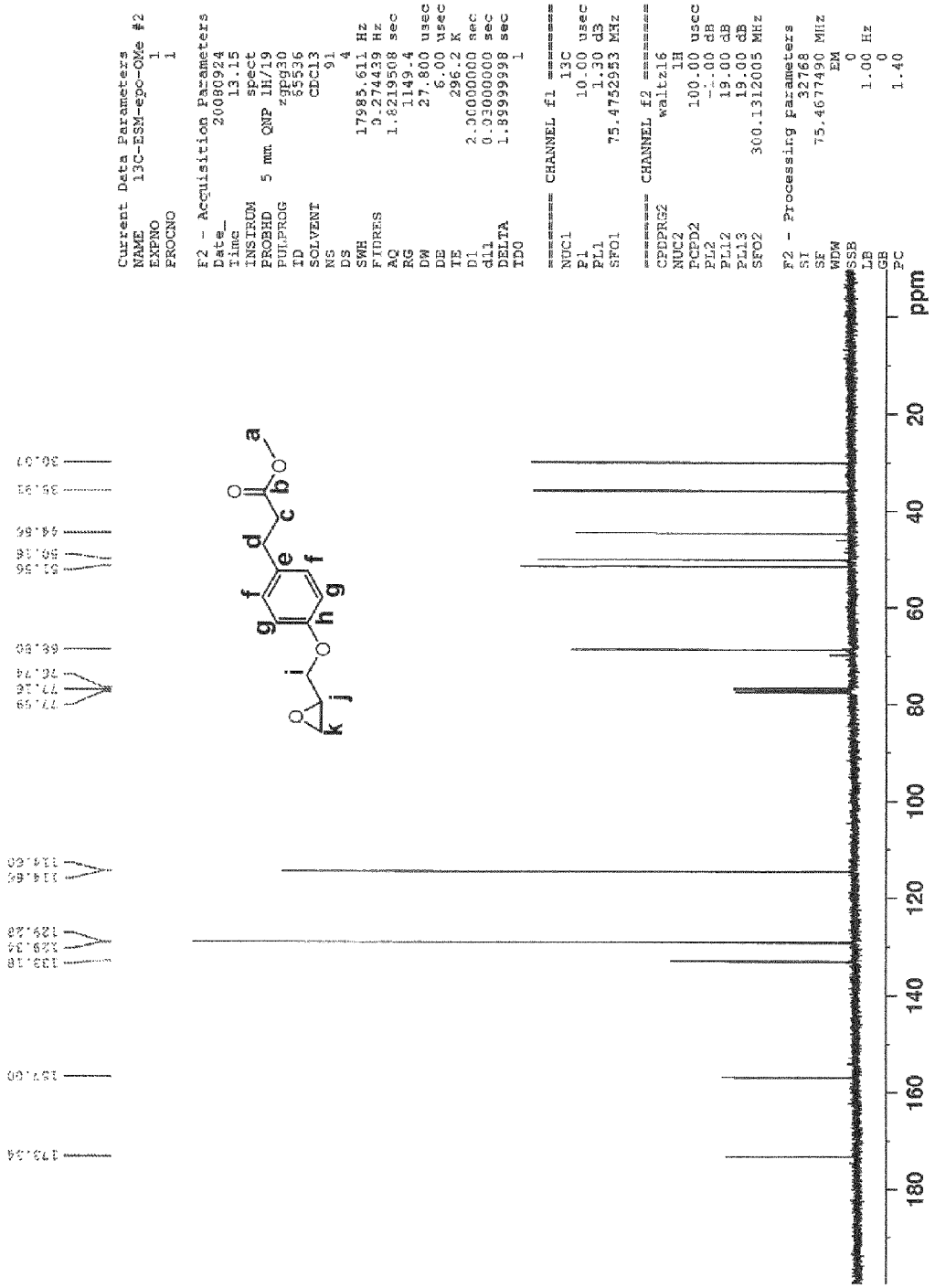
FIG. 2. $^{13}$C-NMR of 4-(oxiranylmethoxy)-benzenepropanoate methyl ester.

In this step, 1011.6 mg (44 mmol) of small sodium metal chips were added to 60 ml of methanol in 100 ml bottle under nitrogen, then the reaction mixture was stirred until all of the sodium metal was dissolved. 7208 mg (40 mmol) of 3-(4-hydroxyphenyl) propionic acid methyl ester put into the upper solution and the mixture was stirred for 1 hour at room temperature 6.26 mL (80 mmol) of epichlorohydrin was added to upper solution at room temperature The mixture was refluxed overnight and the solvent was removed under reduced pressure. The residue was taken up 50 ml of ethyl acetate and was washed with 50 ml water. The organic layer was dried with magnesium chloride anhydrous and was evaporated after filtering. The residue was isolated with column chromatography using gradient solvent system. (hexane:ethyl acetate=10:2 to 10:10) to get 6.196 g of oily product (yield 65%). TLC(SiO2, hexane:ethyl acetate=2:1) Rf value=0.47. 1H-NMR (CDCl3, 300 MHz) δ 7.10(d, 2H, J=8.5 Hz), 6.84(d, 2H, J=8.5 Hz), 4.17-3.93(m, 2H), 3.65(s, 3H), 3.40-3.30(m, 1H), 2.88(t, 2H<J=7.7 Hz), 2.76-2.70(m, 2H), 2.59(t, 2H, J=7.7 Hz). 13C-NMR (CDCl3, 75.8 MHz) δ 171.6, 155.5, 131.7, 127.8, 113.1, 67.3, 50.0, 48.7, 43.2, 34.4, 28.5. The 1-H NMR (FIG. 1) and 13-C NMR (FIG. 2) data were consistent with the assigned structure.

Step 2: Synthesis of ESM

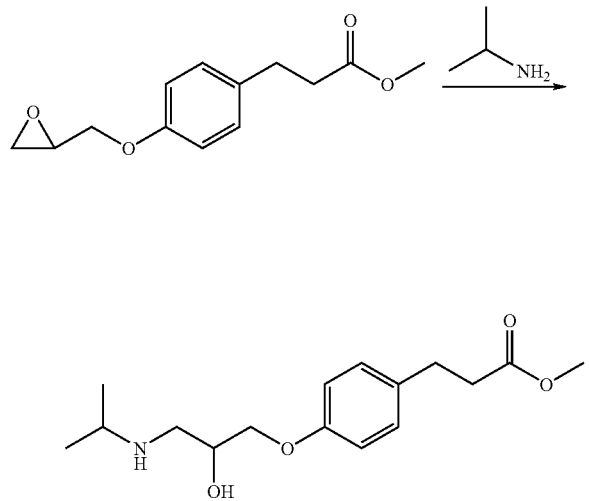

In the above step, the solution of 17 ml (200 mmol) isopropylamine in 15 ml methanol was added to the 4.725 g (20 mmol) of the epoxide compound in 50 ml two neck flask equipped with reflux condenser and calcium chloride tube. Then the reaction mixture was refluxed for 4 hours. The reaction solvent was then evaporated. Resolution oily material was taken up into methanol and treated with etheral HCl and provided crystals to gain 3451.0 mg white powder (yield 52%),. Meanwhile free base reaction mixture was isolated with column chromatography using gradient solvent system (ethyl acetate:methanol=10:2-0:10) Free base:TLC (SiO2, only Methanol) Rf value=0.37. 1H-NMR (CDCl3-, 300 MHz) δ 7.09(d, 2H, J=8.4 Hz), 6.83(d, 2H, J=8.4 Hz), 4.10 (m, 1H), 3.94(d, 2H, J=5.5 Hz), 3.65(s, 3H), 3.05-2.82(m, 4H), 2.73(m, 1H), 2.58(t, 2H, J=7.6 Hz), 1.12(s, 3H), 1.10(s, 3H). 13C-NMR(CDCl3, 75.8 MHz) δ 173.8, 157.6, 133.3, 129.6, 114.9, 72.5, 68.5, 51.9, 49.9, 49.4, 36.3, 30.4, 22.9.

Figure 3:
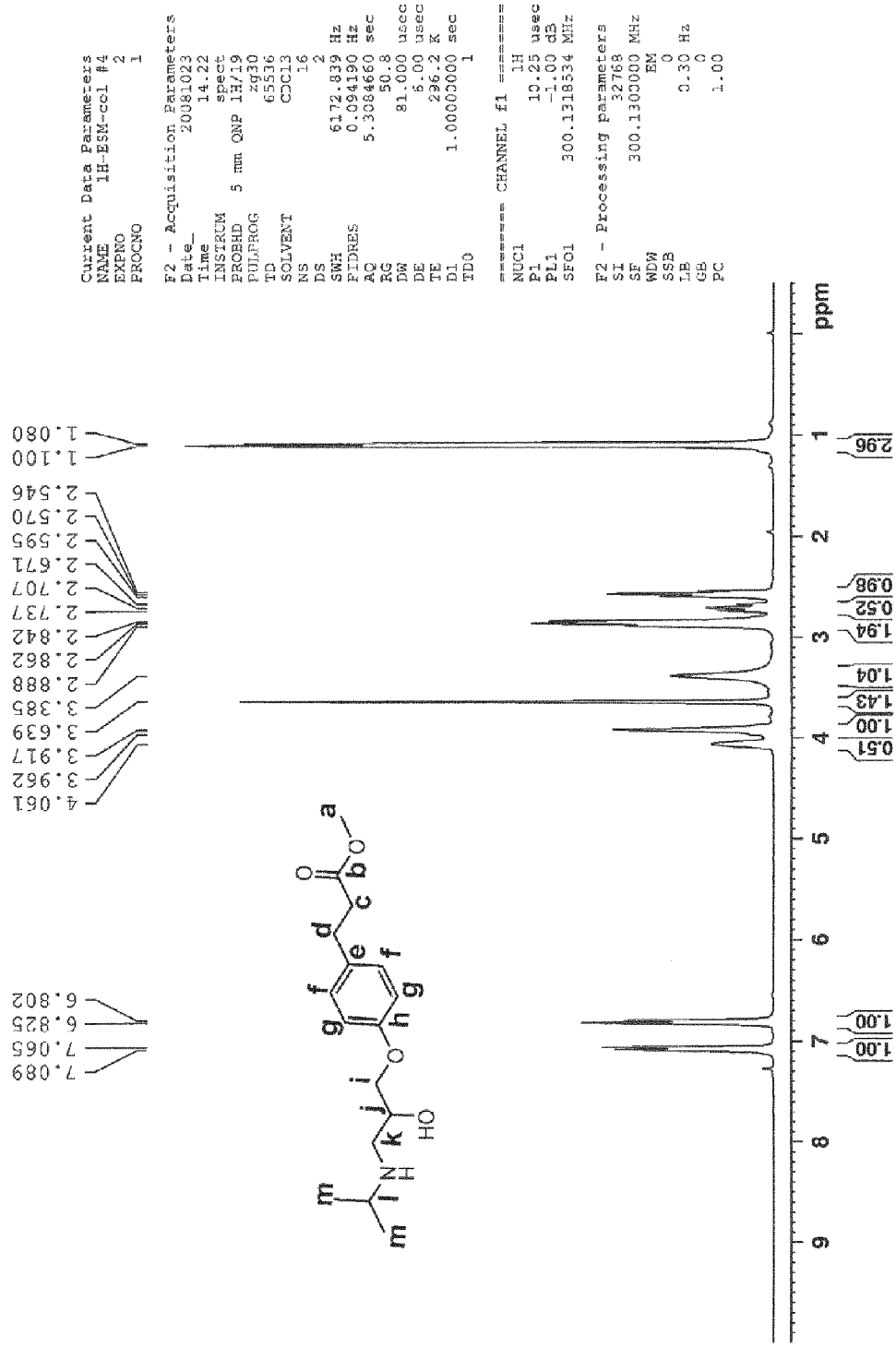
FIG. 3. $^1$H-NMR of ESM.
Figure 4:
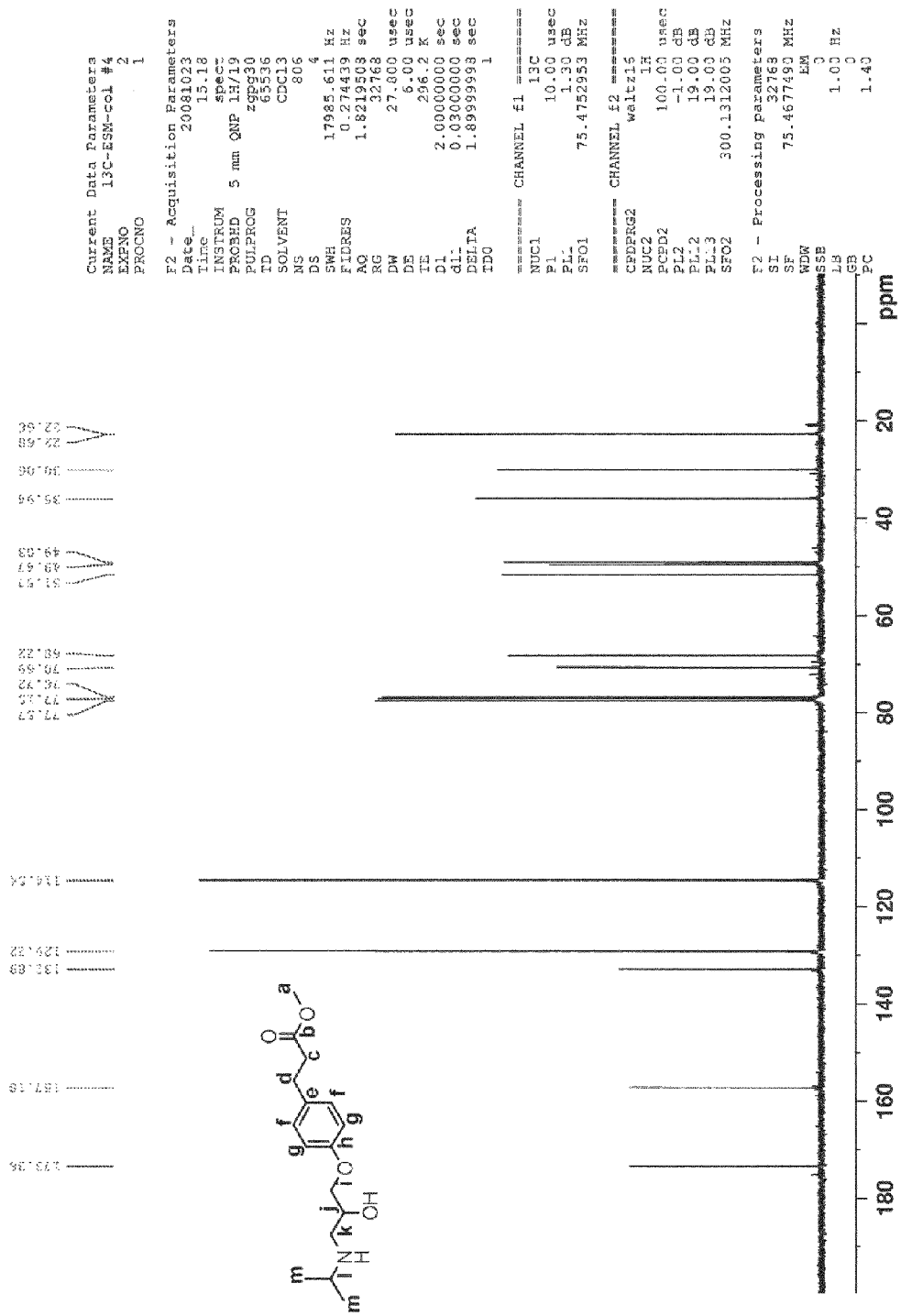
FIG. 4. $^{13}$C-NMR of ESM.

The 1-H NMR (FIG. 3) and 13-C NMR (FIG. 4) data were consistent with the assigned structure, Step 3: Synthesis of EDA-ESM

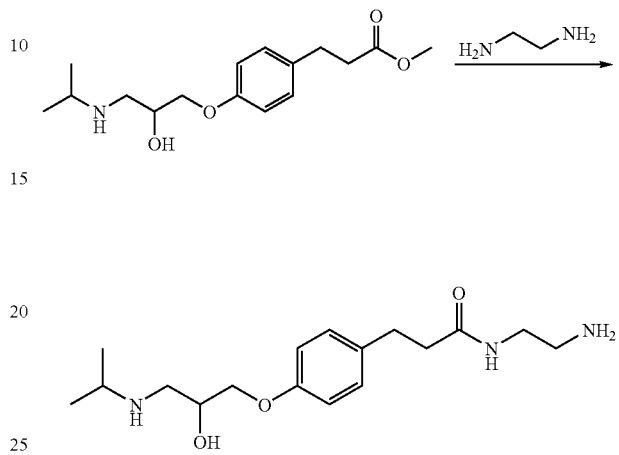

Figure 5:
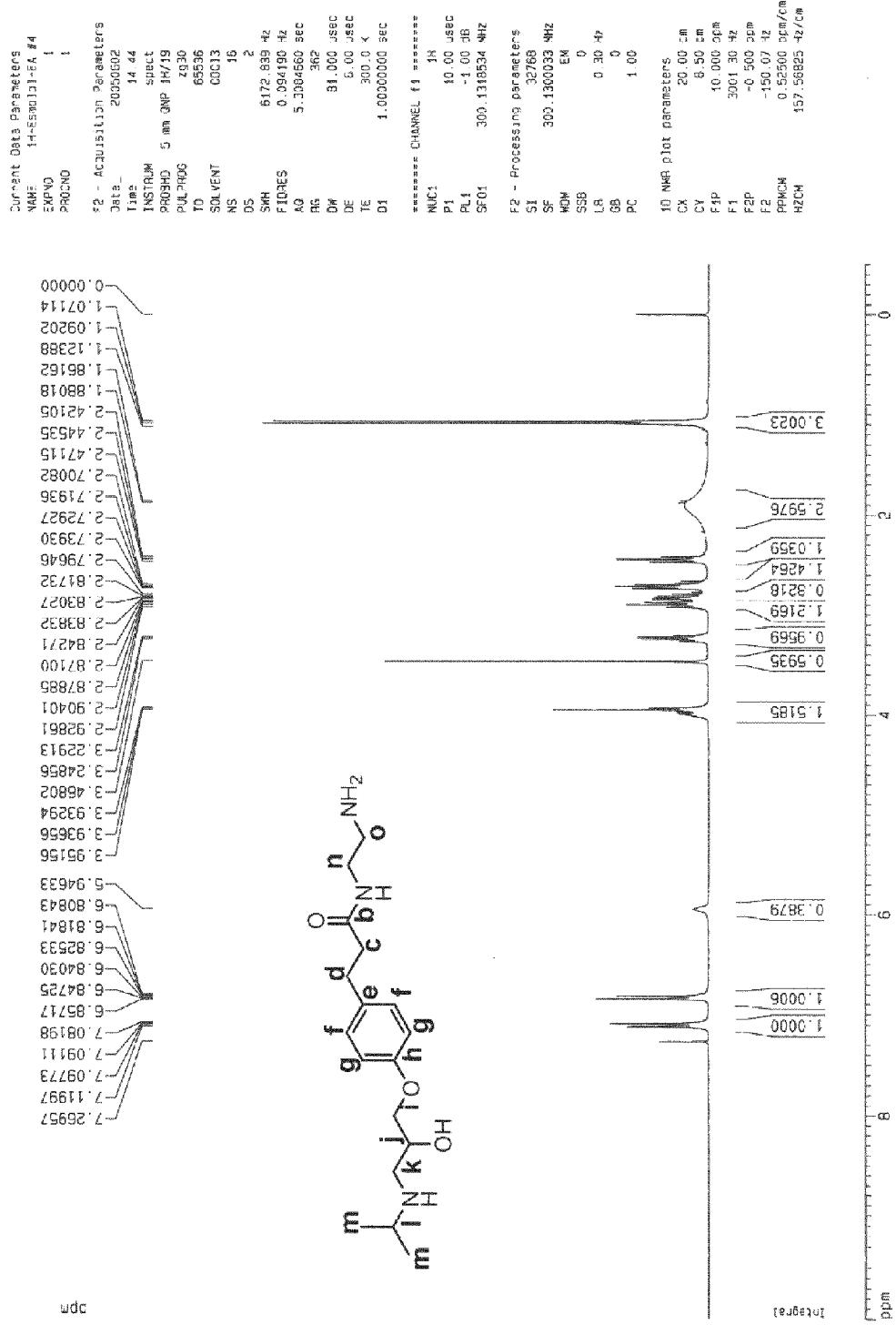
FIG. 5. $^1$H-NMR of EDA-ESM.
Figure 6:
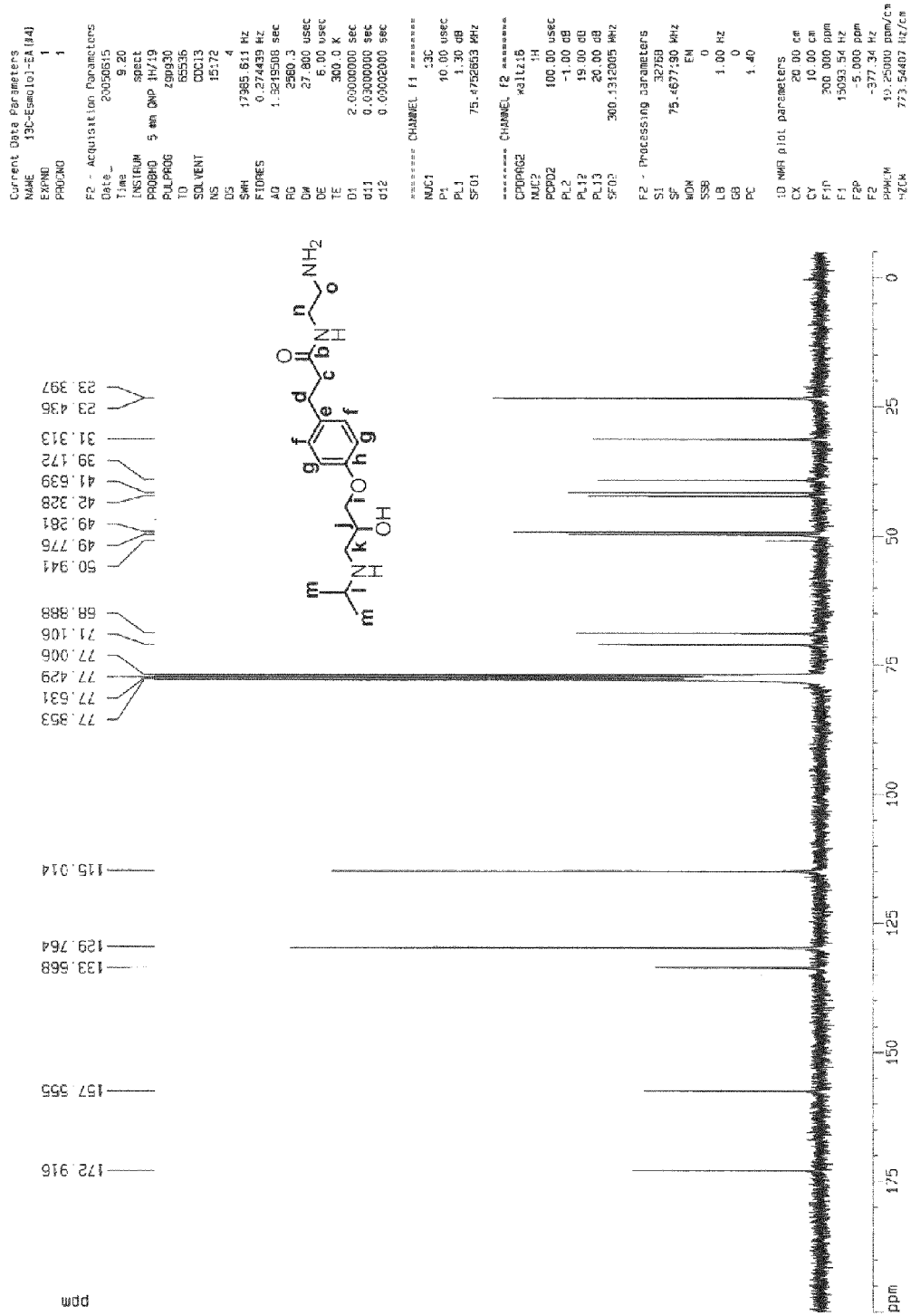
FIG. 6. $^{13}$C-NMR of EDA-ESM.
Figure 7:
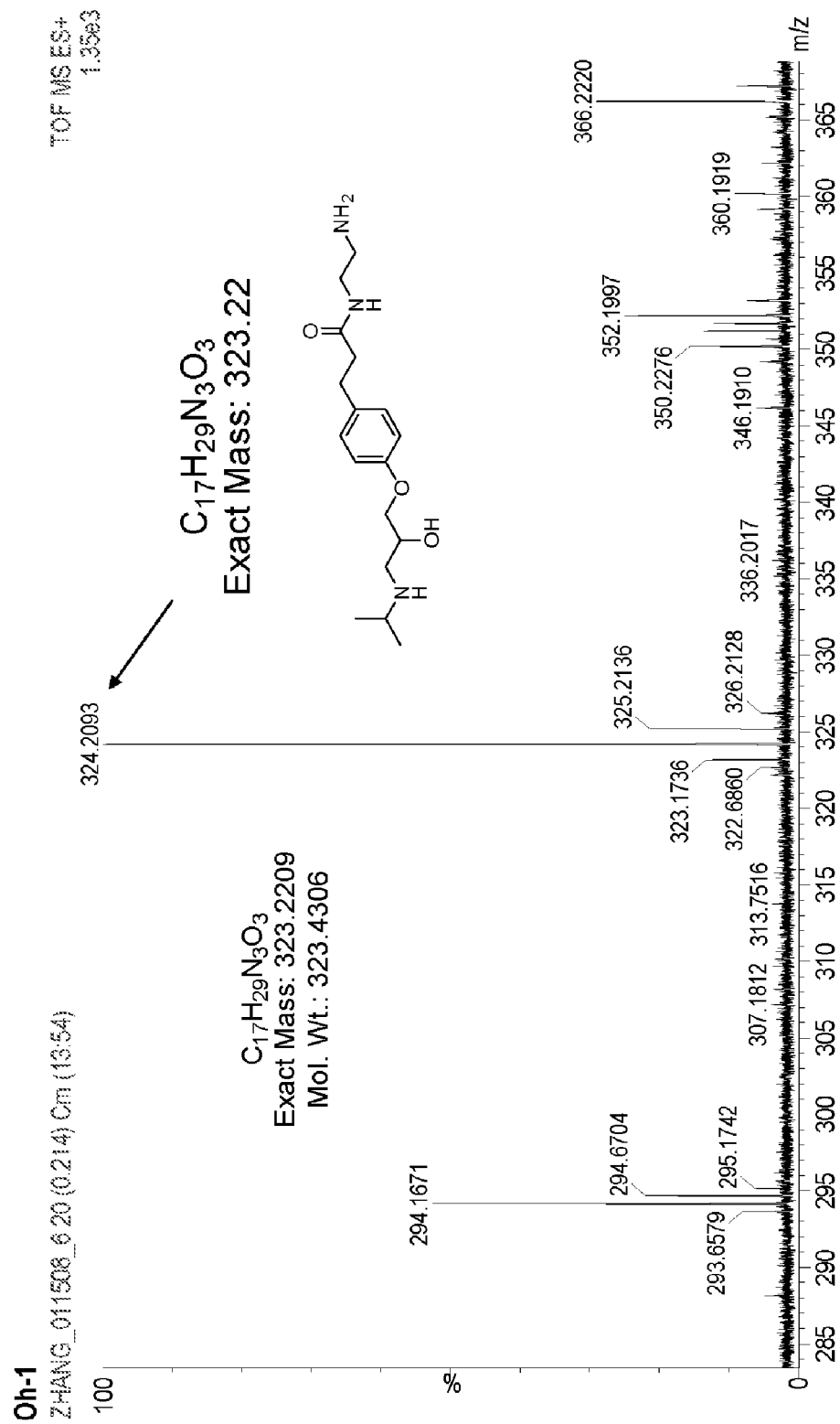
FIG. 7. Mass spectra of EDA-ESM

In Step 3, to the solution of 0.45 ml (6.78 mmol) ethylenediamine in 15 ml methanol in 50 ml two neck flask equipped with reflux condenser and calcium chloride drying tube, 1.0 g (3.39 mmol) of the esmolol was added with stirring then the mixture was refluxed for 8 hours. The reaction medium was evaporated and the residue was dissolved in 10 ml chloroform. The organic layer was washed with water 2 times (2×7 ml) and was dried with magnesium chloride anhydrous. The residue after evaporation of organic layer was isolated with column chromatography using gradient solvent system (methanol:triethyl amime=10:0 to 10:1) to get 954.6 mg of oily material (yield 74.0%). Meanwhile oily material was taken up into methanol and was treated with ehteral HCl to get HCl salt form. Free base: TLC (SiO2, methanol:trietlyh amine=10:1) Rf value=0.44. 1H-NMR (CDCl3-, 300 MHz) δ 7.10(d, 2H, J=8.4 Hz), 6.83(d, 2H, J=8.4 Hz), 5.95(br, 1H), 3.99-3.92(m), 3.47(s), 3.26-3.21(q), 2.80-2.93(m, 5H), 2.66-2.74(m, 5H), 2.42-2.45(m, 2H), 1.09(s, 3H), 1.07(s, 3H). 13C-NMR (CDCl3, 75.8 MHz) δ 172.9, 157.6, 133.7, 129.8, 115.0, 77.6, 71.1, 68.9, 549 8, 49.3, 42.3, 41.6, 39.2, 36.3, 31.3, 23.4. The 1-H NMR(FIG. 5), 13-C NMR (FIG. 6) and Mass spectrum data (FIG. 7) were consistent with the assigned structure Example 2

Radiosynthesis of $^{99m}$Tc-Ethylenediamine-esmolol ($^{99m}$Tc-EDA-ESM)

Figure 8:
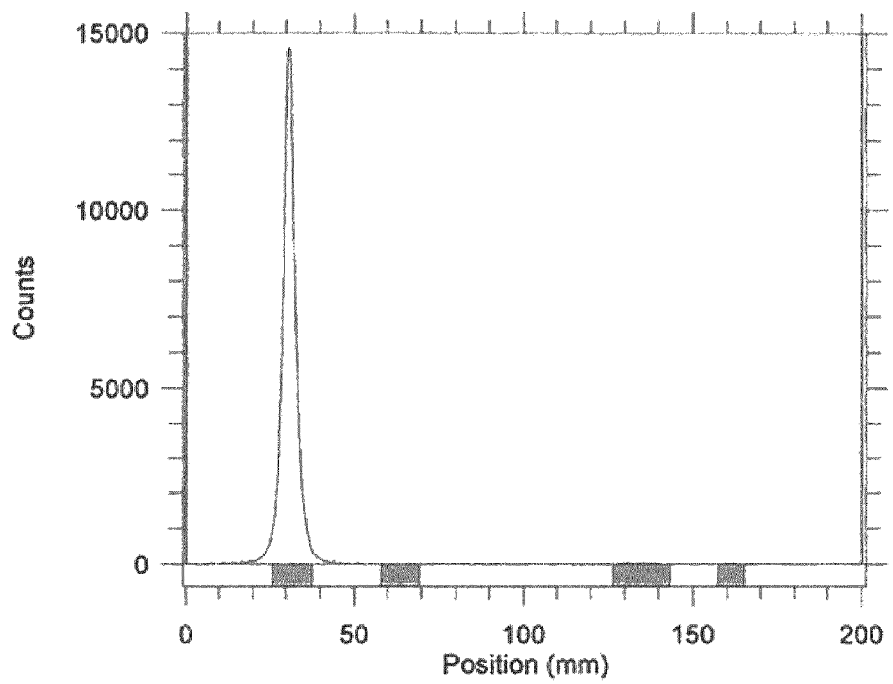
FIG. 8. Radio-TLC analysis of $^{99m}$Tc-EDA-ESM using ammonium acetate (1 M):methanol (4:1) as an eluant. Radiochemical purity was >98%.

EDA-ESM (0.1 mg) was dissolved in 0 2 ml water. Tin (II) chloride (0.1 mg) in 0.1 ml was then added. Na$^{99m}$TcO$_4$ (1 mCi) was then added. Radio-thin layer chromatography using three systems (acetone, saline, 1 M NH$_4$Cl/MeOH(4:1)) was used to analyze the radiochemical purity of $^{99m}$Tc-EDA-ESM. Radiochemical purity of $^{99m}$Tc-EDA-ESM analyzed by these systems showed greater than 98% (FIG. 8) A proposed structure is shown in a scheme below.

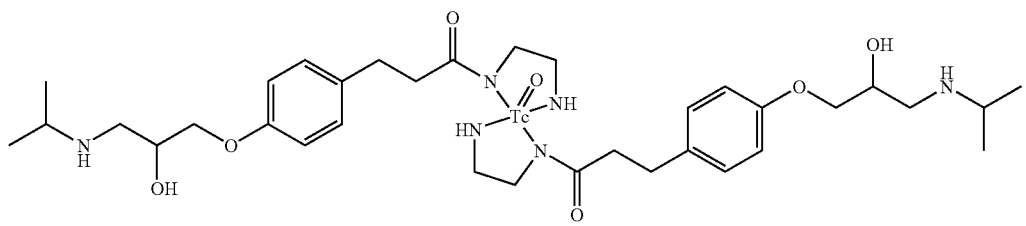

Example 3

Scintigraphic Imaging Studies

Figure 9:
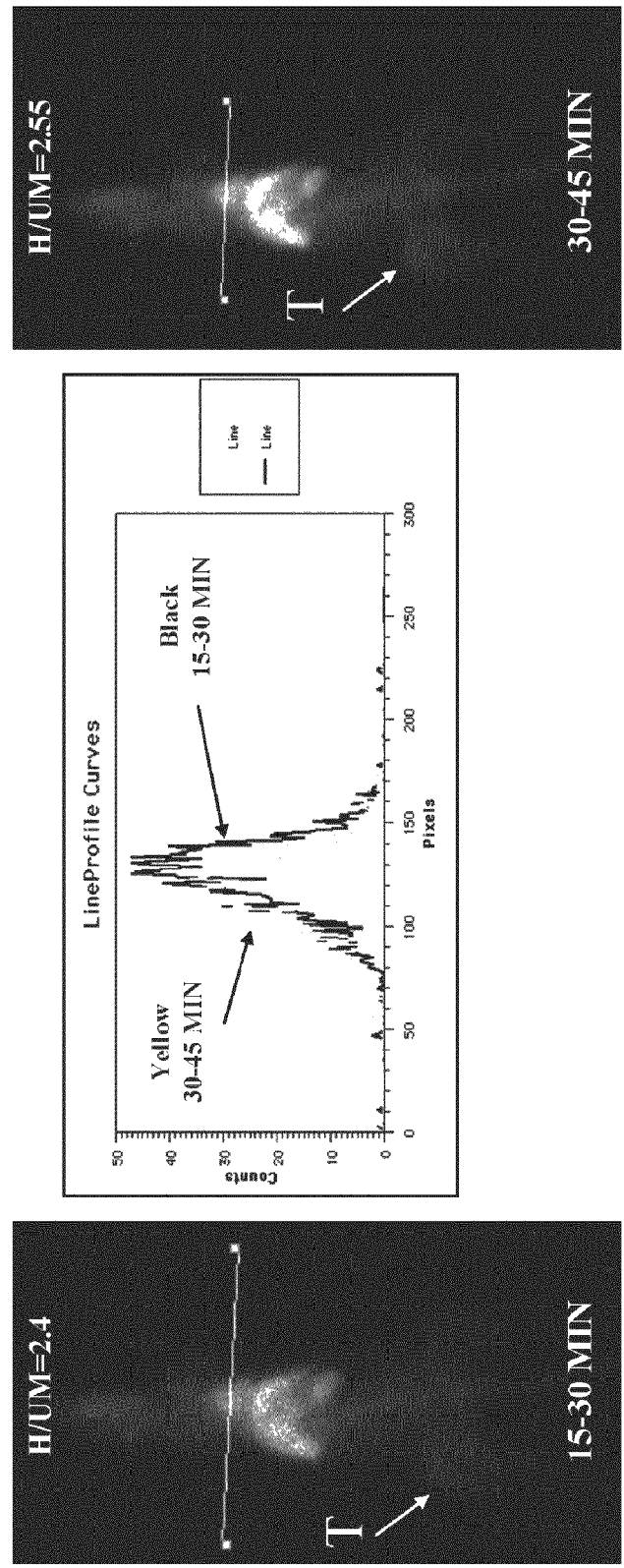
FIG. 9. Planar Images of $^{99m}$Tc-EDA-ESM in Breast Tumor-Bearing Rats. Planar scintigraphy of $^{99}$mTc-EDA-ESM (300 µCi/rat) in breast tumor-bearing rats acquired at 15-45 minutes. The numbers are Heart/Upper mediastinum count density (counts/pixel) ratios. The line profile curve demonstrated high cardiac region count/pixels ratio compared to laterally located tissues.
Figure 10:
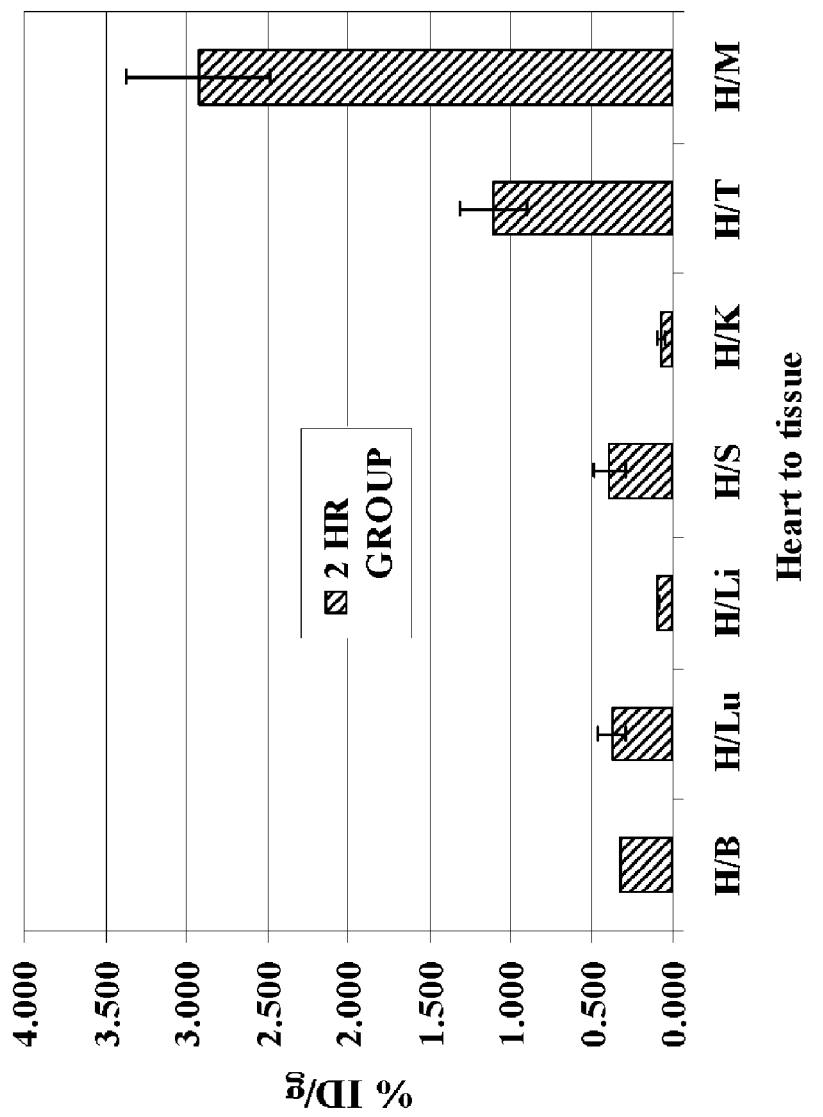
FIG. 10. Heart to Tissue Count Density ratio of $^{99m}$Tc-EDA-ESM in Breast Tumor Bearing Rats (n=4 300 pCi/rat, IV). Heart/organ ratios after the rats were sacrificed at 2 hrs (B: blood; Lu: lung; Li: liver; S: stomach; K: kidney; T: tumor; M: muscle).
Figure 11:
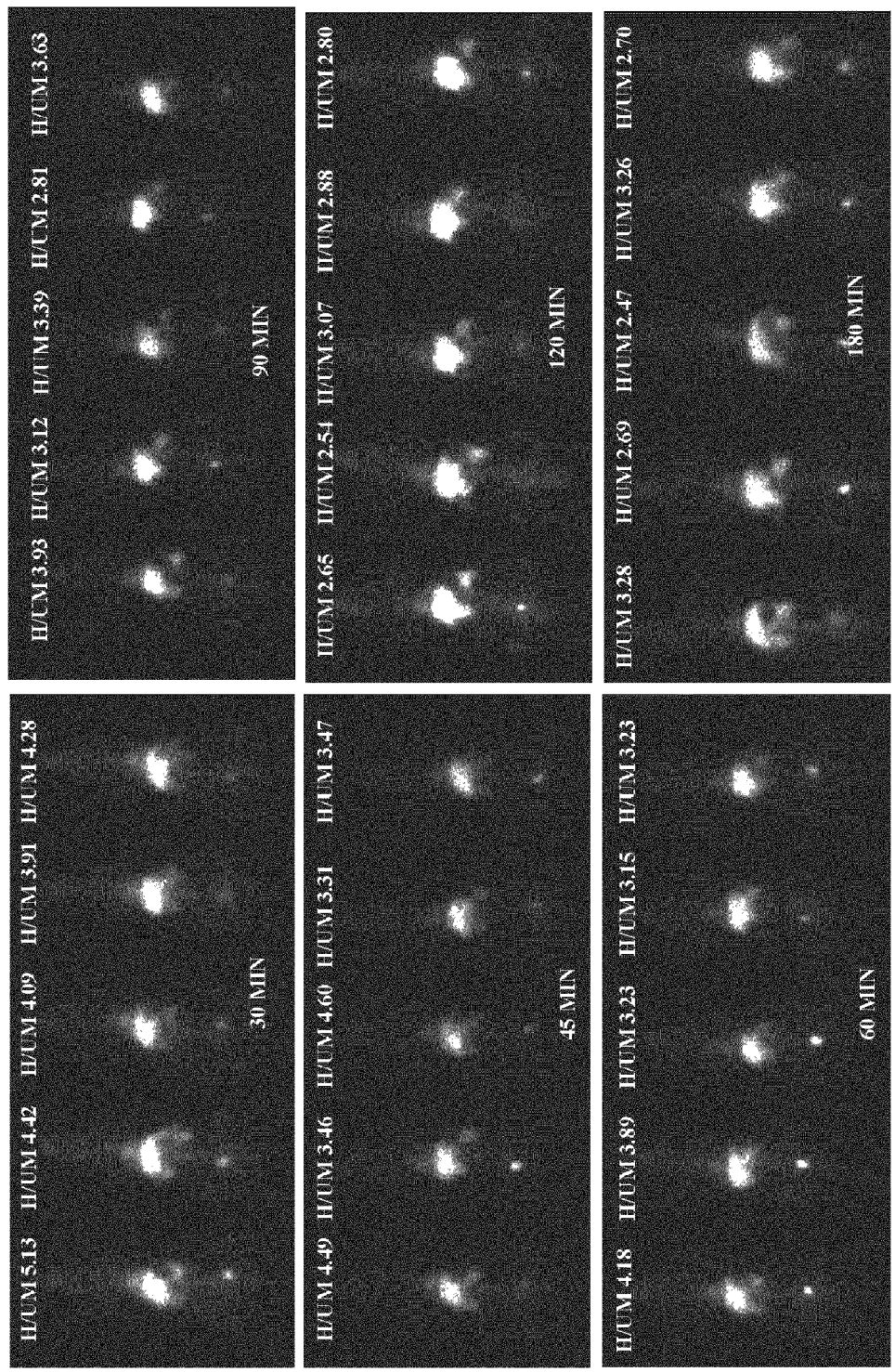
FIG. 11. 20-180 min Planar Images of $^{99m}$Tc-EDA-ESM in normal rats.
Figure 12:
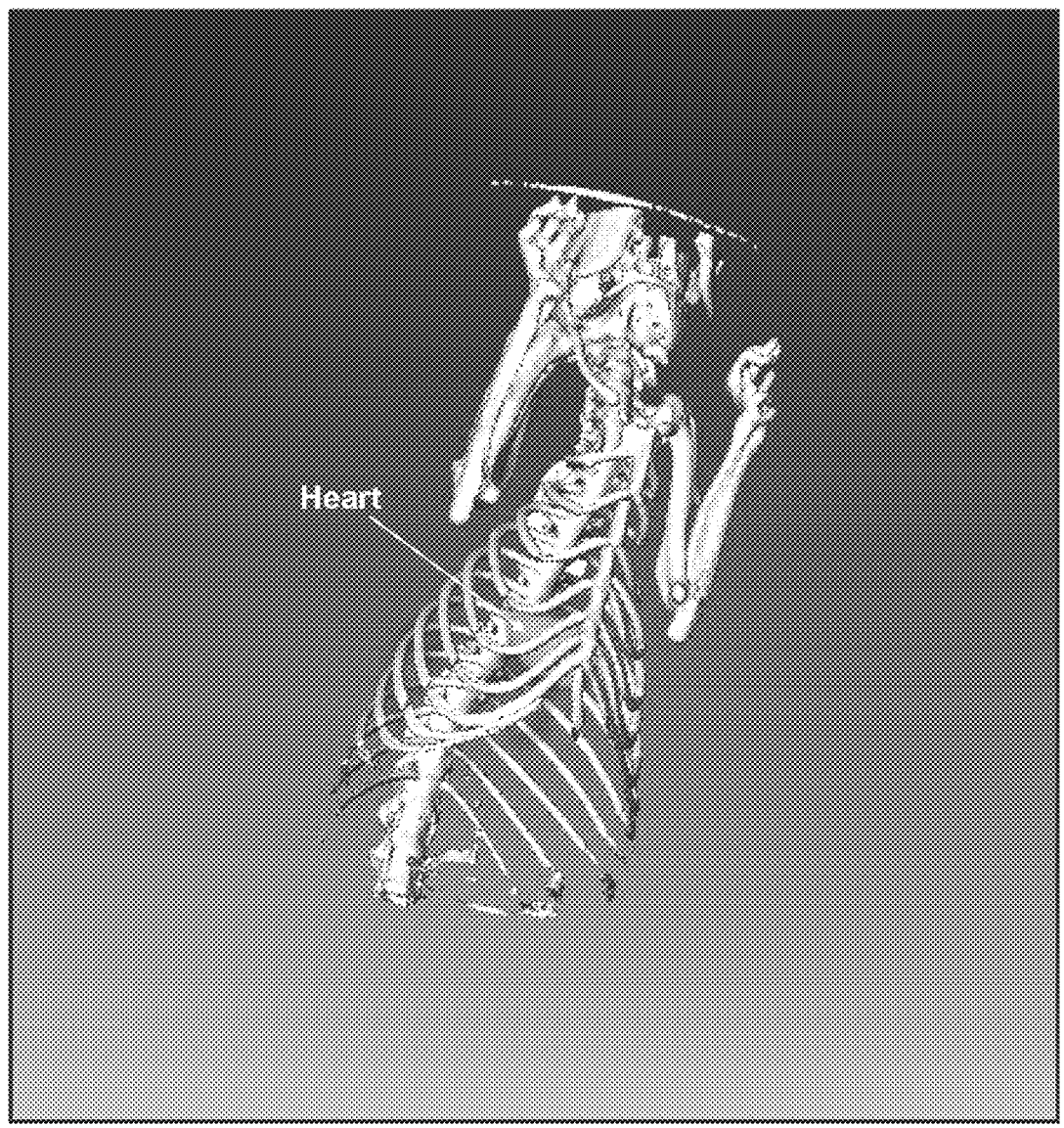
FIG. 12. SPECT/CT of $^{99m}$Tc-EDA-ESM.

To ascertain $^{99m}$Tc-EDA-ESM is a heart-specific agent, not tumor seeking agent, the inventors created a tumor model. Female Fischer 344 rats (125-175 g, n=5) were inoculated with breast cancer cells (13762NF, $10^6$ cells/rat, s.c. in the hind leg). After 15-20 days and a tumor volume of 1 cm, the breast tumor-bearing rats were administered with 300 µCi of $^{99m}$Tc-EDA-ESM. Scintigraphic images, using a gamma camera equipped with low-energy, parallel-hole collimator, were obtained from 15 to 45 min. In separate studies, normal Female Fischer 344 rats (150-1759, n=5) were administered with 300 µCi of $^{99m}$Tc-EDA-ESM and scintigraphic images were obtained at 30-180 min. One rat was administered with 300 µCi of $^{99m}$Tc-EDA-ESM and SPECT/CT was performed at 45 min. In rats administered with $^{99m}$Tc-EDA-ESM, the selected image from one tumor-bearing rat is shown in FIG. 9. The tumor could not be visualized well; however, heart had high uptake. Heart to muscle (H/M) count density uptake ratios obtained from tumor-bearing rats (n=4) were higher than other tissues (FIG. 10). In normal rats administered with $^{99m}$Tc-EDA-ESM (n=5), heart to muscle (HIM) count density uptake ratios were increased (2.7 to 5.1) at 30-180 min (FIG. 11). SPECT/CT images of a normal rat showed high heart uptake (FIG. 12).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,387,103
U.S. Pat. No. 4,439,356
U.S. Pat. No. 5,188,934
U.S. Pat. No. 6,521,209
U.S. Pat. No. 6,770,259
Alberico et al., *Surg. Oncol. Clin. N. Am.*, 13(1):13-35, 2004.
Deng and Lizzi, *Ultrasound Med. Biol.*, 28(3):277-286, 2002.
Erhardt et al., *J Med. Chem.*, 25:1408-1412, 1982.
Forsberg et al., *Ultrasound Med. Biol.*, 23(8):1201-1208, 1997.
Goldberg et al., *Ultrasound Med. Biol.*, 20(4):319-333, 1994.
Goldberg, *Heart*, 78(3):209-210, 1997.
Henson et al., *AJNR Am. J. Neuroradiol.*, 25(6):969-972, 2004.
Ophir and Parker, *Ultrasound Med. Biol.*, 15(4):319-333, 1989.
PCT Appln. PCT/US90/05565
PCT Appln. WO 2004/026344
Remington's Pharmaceutical Sciences, 21th Ed. Lippincott Williams & Wilkins, 2005.
Ronda et al., *Reactive & Functional Polymers*, 28:1-11, 1995.
Saha et al., *Semin. Nucl. Med.*, 24(4):324-349, 1994.
Strunk and Schild, *Eur. Radiol.*, 14(6):1055-1062, 2004.
European Patent Application 87310256.0

What is claimed is:

1. An imaging agent comprising a beta-adrenergic receptor ligand conjugated to a terminal nitrogen of a polyethylene amine derived chelator.

2. The agent of claim 1, wherein the beta-adrenergic receptor ligand is selected from the group consisting of AC 623, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, butidrine hydrocholoride, butofilolol, carazolol, carteolol, carvedilol, celiprolol, cetamolol, cloranolol, dilevalol, esmolol, indenolol, labetalol, landiolol, levobunolol, mepindolol, metipranolol, metoprolol, moprolol, nadolol, nadoxolol, nebivolol, nifenalol, nipradilol, oxprenolol, penbutolol, pindolol, practolol, pronethalol, propranolol, sotalol, sulfinalol, talinolol, tertatolol, tilisolol, timolol, toliprolol, xibenolol and combinations thereof.

3. The agent of claim 2, wherein the beta-adrenergic receptor ligand is esmolol.

4. The agent of claim 1, further comprising a valent metal ion chelated to the polyethylene amine derived chelator.

5. The agent of claim 4, wherein the valent metal ion is selected from the group consisting of Gd, Fe, Tc-99m, Cu-60, Cu-61, Cu-62, Cu-64, Cu-67, In-111, Tl-201, Ga-67, Ga-68, As-72, Re-186, Re-188, Ho-166, Y-90, Sm-153, Sr-89, Bi-212, and Bi-213.

6. The agent of claim 4, wherein the valent metal ion is selected from the group consisting of a therapeutic metal selected from the group consisting of arsenic, cobolt, copper, selenium, thallium, and platinum.

7. The agent of claim 1, further comprising an imaging moiety.

8. The agent of claim 7, wherein the imaging moiety is a contrast media.

9. The agent of claim 8, wherein the contrast media is selected from the group consisting of a CT contrast media, an MRI contrast media, and optical contrast media, and an ultrasound contrast media.

10. A method of imaging a subject having a cardiovascular disease, comprising:
   a) administering to the subject a composition comprising an effective amount of an agent in accordance with claim 1; and
   b) performing imaging using a first imaging modality by detecting a first signal from said agent; and
   c) performing imaging using a second imaging modality by detecting a second signal from said agent,
wherein the first imaging modality and the second imaging modality are performed either concurrently or consecutively.

11. The method of claim 10, wherein the first imaging modality and the second imaging modality are each selected from the group consisting of PET, CT, SPECT, MRI, optical imaging, and ultrasound.

12. The method of claim 10, wherein the first imaging modality and the second imaging modality are identical.

13. A kit for preparing a diagnostic or therapeutic composition comprising a sealed container including a predetermined quantity of an agent in accordance with claim 1.

14. The kit of claim 13, further comprising a radionuclide selected from the group consisting of Tc-99m, Cu-60, Cu-61, Cu-62, Cu-67, In-111, Tl-201, Ga-67, Ga-68, As-72, Re-188, Ho-166, Y-90, Sm-153, Sr-89, Gd-157, Bi-212, and Bi-213.

15. The agent of claim 1, wherein the polyethylene amine derived chelator is a diethylenetriamine, triethylenetetramine, tetraethylenepentamine, pentaethylenehexamine or ethylenediamine chelator.

16. The method of claim 15, wherein the polyethylene amine derived chelator is a ethylenediamine chelator.

17. The agent of claim 16, wherein the beta-adrenergic receptor ligand is esmolol.

* * * * *